United States Patent
Hildebrand et al.

(10) Patent No.: US 7,232,435 B2
(45) Date of Patent: *Jun. 19, 2007

(54) DELIVERY OF A SYMPATHOLYTIC CARDIOVASCULAR AGENT TO THE CENTRAL NERVOUS SYSTEM TO COUNTER HEART FAILURE AND PATHOLOGIES ASSOCIATED WITH HEART FAILURE

(75) Inventors: Keith R. Hildebrand, Houlton, WI (US); Michael R. Ujhelyi, Maple Grove, MN (US); Xiaohong Zhou, Plymouth, MN (US); Daniel C. Sigg, St. Paul, MN (US); Linda M. Page, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 175 days.

This patent is subject to a terminal disclaimer.

(21) Appl. No.: 10/773,965

(22) Filed: Feb. 6, 2004

(65) Prior Publication Data

US 2005/0177135 A1 Aug. 11, 2005

(51) Int. Cl.
*A61K 9/22* (2006.01)
(52) U.S. Cl. .............................. 604/891.1; 604/890.1; 604/66; 604/500; 604/503; 604/508
(58) Field of Classification Search ................ 604/82, 604/508, 890.1, 891.1, 892.1, 500, 503, 66; 424/426; 128/898
See application file for complete search history.

(56) References Cited

U.S. PATENT DOCUMENTS

| 4,263,679 A | 4/1981 | Erlendson |
| 4,603,141 A | 7/1986 | Giles |
| 4,692,147 A | 9/1987 | Duggan |
| 4,987,897 A | 1/1991 | Funke |
| 5,269,301 A | 12/1993 | Cohen |
| 5,330,505 A | 7/1994 | Cohen |

(Continued)

OTHER PUBLICATIONS

Buerkle et al. "Thermal and mechanical antiocicipetive action of spinal vs peripherally administered clonidine in the rat inflamed knee joint model." British Journal of Anasthesia 1999; 83(3); 436-41.*

(Continued)

*Primary Examiner*—Kevin C. Sirmons
*Assistant Examiner*—Catherine N. Witczak
(74) *Attorney, Agent, or Firm*—Paul H. McDowall; Girma Wolde-Michael

(57) ABSTRACT

A sympatholytic cardiovascular agent delivered by a drug delivery pump to a central nervous system site to alleviate symptoms and otherwise treat heart failure (HF) and pathologies associated with HF. The drug delivery pump can be external or implantable infusion pump (IIP) coupled with a drug infusion catheter extending to the site. A patient activator can command delivery of a dosage and/or an implantable heart monitor (IHM) coupled with a sensor can detect physiologic parameters associated with HF (or pathologies associated with HF) and trigger dosage delivery. The IIP and IHM can be combined into a single implantable medical device (IMD) or can constitute separate IMDs that communicate by any of known communication mechanisms. The sympatholytic cardiovascular agent is one of the group consisting of an alpha-adrenergic agonist and an alpha2-adrenergic agonist, e.g., clonidine, p-aminoclonidine, guanabenz, lidamidine, tizanidine, moxonidine, methyldopa, xylazine, guanfacine, detomidine, medetomidine, and dexmedetomidine.

37 Claims, 11 Drawing Sheets

U.S. PATENT DOCUMENTS

| | | | |
|---|---|---|---|
| 5,331,966 A | 7/1994 | Bennett et al. | |
| 5,368,040 A | 11/1994 | Carney | |
| 5,417,717 A | 5/1995 | Salo et al. | |
| 5,564,434 A | 10/1996 | Halperin | |
| 5,643,207 A | 7/1997 | Rise | |
| 5,674,249 A | 10/1997 | de Coriolis et al. | 607/5 |
| 5,755,737 A | 5/1998 | Prieve et al. | |
| 5,782,798 A | 7/1998 | Rise | |
| 5,801,188 A | 9/1998 | Hassenbusch, III et al. | 514/392 |
| 5,807,243 A | 9/1998 | Vierra et al. | |
| 5,810,735 A | 9/1998 | Halperin | |
| 5,893,881 A | 4/1999 | Elsberry et al. | 607/5 |
| 5,919,210 A | 7/1999 | Lurie et al. | |
| 6,104,949 A | 8/2000 | Pitts Crick et al. | |
| 6,128,537 A * | 10/2000 | Rise | 607/45 |
| 6,280,409 B1 | 8/2001 | Stone et al. | |
| 6,438,408 B1 | 8/2002 | Mulligan et al. | |
| 2001/0027309 A1* | 10/2001 | Elsberry | 604/508 |
| 2001/0037083 A1* | 11/2001 | Hartlaub et al. | 604/65 |
| 2002/0107553 A1 | 8/2002 | Hill et al. | |
| 2002/0120205 A1 | 8/2002 | Ferek-Petric | |
| 2002/0143369 A1 | 10/2002 | Hill et al. | |
| 2002/0149155 A1 | 10/2002 | Schmauder | |
| 2002/0165586 A1 | 11/2002 | Hill et al. | |
| 2003/0004549 A1 | 1/2003 | Hill et al. | 607/9 |
| 2003/0045805 A1 | 3/2003 | Sheldon et al. | |
| 2003/0083702 A1 | 5/2003 | Stadler | |
| 2003/0100925 A1 | 5/2003 | Pape et al. | |
| 2003/0149450 A1* | 8/2003 | Mayberg | 607/3 |
| 2003/0204181 A1 | 10/2003 | Starkebaum | |
| 2004/0073197 A1* | 4/2004 | Kim | 604/891.1 |
| 2004/0162497 A1 | 8/2004 | Bennett | |
| 2004/0167410 A1 | 8/2004 | Hettrick | |

OTHER PUBLICATIONS

Hunt et al., "ACC/AHA Guidelines for the Evaluation and Management of Chronic Heart Failure in the Adult: Executive Summary", J. Am. Coll. Cardiol., 38(7): 2101-2113, 2001.

Giles, et al., "Acute Effects of Intravenous Clonidine HCl in Congestive Heart Failure", Circulation II, 62(4) Oct. 1980.

Eisenach, Anethesiology, 74: 766-771, 1991.

Azeuedo et al., J. Am. Coll. Cardiol., 33(1): 186-91, 1999.

Esler et al., J. Auton. Nervous Sys., 72(2-3): 210-9, 1998.

Manolis et al., Clin. Exp. Hypertens, 20(7): 717-31, 1998.

Zhang et al., J. Cardiol., 65(3): 233-8, 1998.

Girgis et al., Am. J. Cardiol., 82(3): 335-7, 1998.

Zhang et al., Int. J. Cardiol., 59(2):139-44, 1997.

* cited by examiner

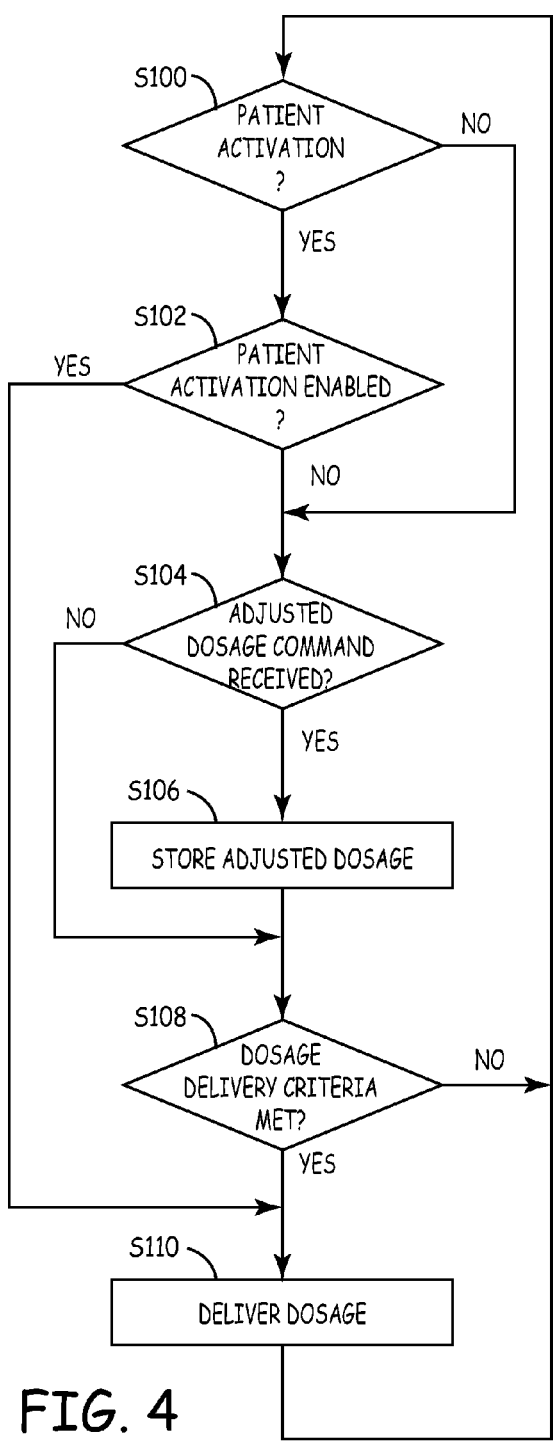
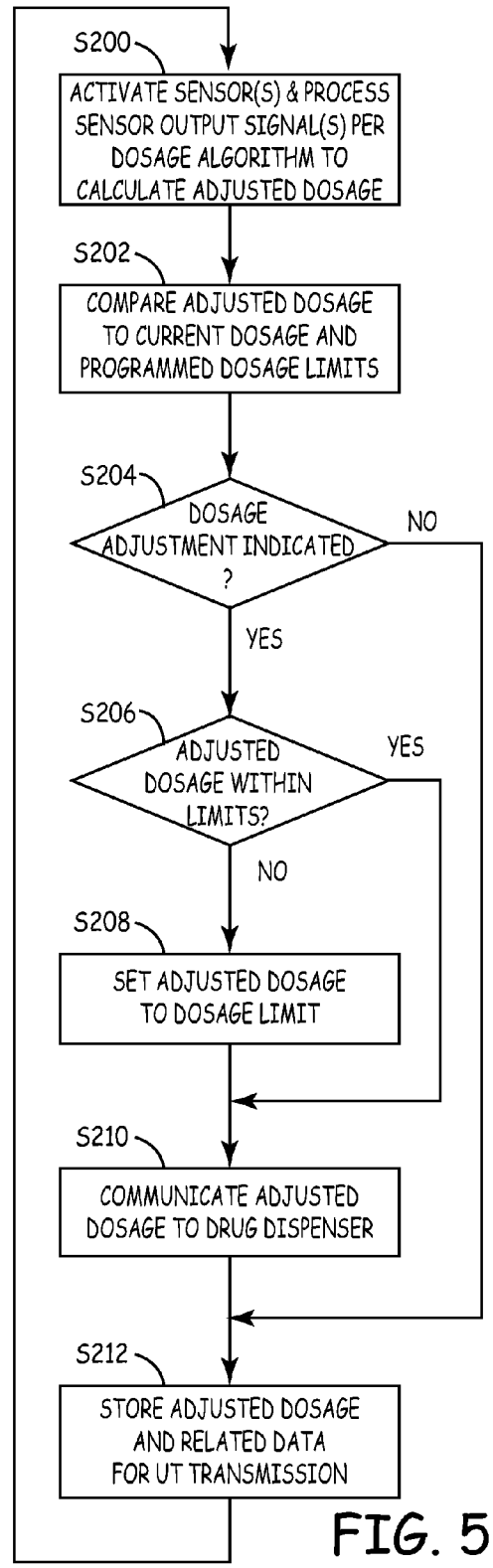
FIG. 4
FIG. 5

DELIVERY OF A SYMPATHOLYTIC CARDIOVASCULAR AGENT TO THE CENTRAL NERVOUS SYSTEM TO COUNTER HEART FAILURE AND PATHOLOGIES ASSOCIATED WITH HEART FAILURE

FIELD OF THE INVENTION

This invention relates to implantable medical devices (IMDs), and particularly to an implantable heart monitor (IHM) coupled with at least one sensor for detecting symptoms of heart failure (HF) or pathologies associated with HF and triggering delivery by a drug dispenser of a sympatholytic cardiovascular agent to a central nervous system site to alleviate such symptoms and otherwise treat HF and pathologies associated with HF.

BACKGROUND OF THE INVENTION

Generally speaking, the practice of medicine involves the diagnosis of a human disease from observed symptoms to develop a disease or injury hypothesis, the prescription and administration of a therapeutic treatment, e.g., a drug regimen and/or other therapy, the monitoring of the patient's adherence to self-administered treatment, particularly a drug regimen, the periodic assessment of the efficacy or lack of efficacy of the treatment, and the revision of the prescription and administration as necessary. The present invention is related to these practices in the particular context of assessing, monitoring and treating cardiac diseases, particularly those exhibiting pathologies associated with HF.

Pathologies Associated With Heart Failure:

The term "heart failure" (HF) as used herein embraces congestive heart failure (CHF) and/or chronic heart failure as defined by the American College of Cardiology and the American Heart Association as set forth in a report of the American College of Cardiology/American Heart Association Task Force on Practice Guidelines (Committee to revise the 1995 Guidelines for the Evaluation and Management of Heart Failure) authored by Hunt et al. See "ACC/AHA guidelines for the evaluation and management of chronic heart failure in the adult: executive summary", J Am Coll Cardiol 2001; 38(7): 2101–2113). For convenience, HF is used herein to embrace CHF and other chronic heart failure states.

In addition, "pathologies associated with HF" is defined herein as including the pathologies described below that either accompany HF or are or can be precursors to or causative of the progression of cardiac disorders to HF. In this regard, almost any cardiac disorder that impairs the ability of the ventricles to eject blood exhibits a progression toward an inexorable deterioration of cardiac structure and function, producing the complex clinical syndrome of HF. It is estimated that perhaps as many as 20 million individuals in the United States have an asymptomatic impairment of cardiac function and are likely to develop symptoms of chronic HF in the next 1 to 5 years. Such asymptomatic or symptomatic impairments of cardiac function that often accompany or progress to HF include angina, coronary artery disease, cardiac arrhythmias high blood pressure (hypertension), ischemic heart disease, exposure to cardiotoxic compounds, such as the anthracycline antibiotics, genetic defects, infarct or idiopathic cardiomyopathy. The early identification and appropriate treatment of such individuals is highly desirable to achieve the greatest impact on individual and public health.

In early stages of HF, the increased workload that results from hypertension or loss of contractile tissue induces compensatory cardiomyocyte hypertrophy and thickening of the left ventricular wall, thereby enhancing contractility and maintaining cardiac function. However, over time, the left ventricular chamber dilates resulting in the general weakening of the contractile function of the cardiac muscle and impairment of myocardial relaxation in the diastolic phase following contraction. Left ventricular end-diastolic volume remains normal due to a decrease in left ventricular compliance concomitant with increased ventricular wall stiffness. Systolic pumping function therefore deteriorates, and the cardiomyocytes undergo apoptotic cell death. The hearts of patients who have progressed to HF manifest an elevation of left ventricular end-diastolic pressure, according to the well-known heterometric autoregulation principles espoused by Frank and Starling.

HF is also associated with increased activity of the sympathetic nervous system and defective parasympathetic control and activation of numerous neurohumoral mechanisms for retention of salt and water. These neurohumoral mechanisms include the renin-angiotensin system and antidiuretic hormone. Although it is clear that the principal disturbance in HF is the inability of the heart to perform as a pump, the clinical picture is often dominated by alterations of the systemic and pulmonary circulations resulting from the intense disturbance of autonomic function. In fact, these disturbances account for many of the symptoms associated with HF including pulmonary edema, shortness of breath, and disruption in systemic blood pressure. Furthermore, the heart is prevented from returning to a more normal state because these compensatory mechanisms are present even when the body is at rest. All these disease processes lead to insufficient cardiac output to sustain mild or moderate levels of exercise and proper function of other body organs. The progressive deterioration eventually results in cardiogenic shock, arrhythmias, electromechanical dissociation, and death.

Drug Regimens:

Patients suffering from HF and such pathologies associated with HF are normally treated with drug therapies including a "cardiovascular agent", that is, a compound that has been found to be useful and "suitable" to treat one or more abnormal conditions associated with the pulmonary or cardiovascular system. Known cardiovascular agents or drugs are listed in U.S. Patent Application 2002/0049155 published Apr. 25, 2002, including blood modifiers, adrenergic blockers (peripheral), adrenergic stimulants (central), alpha/beta adrenergic blockers, angiotensin converting enzyme (ACE) inhibitors, angiotensin II receptor antagonists, anti-arrhythmics (groups I, II, III and IV), miscellaneous anti-arrhythmics, 30 anti-lipemic agents, beta adrenergic blocking agents, calcium channel blockers, diuretics, hypertensive emergency agents, inotropic agents, miscellaneous cardiovascular agents, rauwolfia derivatives, vasodilators and vasopressors. It is further stated that preferred modes of administration of at least certain of drug therapies are parenteral, intraperitoneal, intravenous, intradermal, epidural, intraspinal, intrasternal, intra-articular, intra-synovial, intrathecal, intra-arterial, intracardiac, intramuscular, intranasal, subcutaneous, intraorbital, intracapsular, topical, transdermal patch, via rectal, vaginal or urethral administration including via suppository, percutaneous, nasal spray, surgical implant, internal surgical paint, infusion pump or via catheter. However, the particular modes of administration are not associated with particular cardiovascular agents.

The sympathetic division of the autonomic nervous system plays a major role in affecting cardiovascular function in both health and disease. Recently, it has been appreciated that what may begin as a short-term beneficial compensatory response by the sympathetic nervous system to HF, may lead to de-compensation and worsening of the disease state if this increased sympathetic output is prolonged. The deleterious role of the sympathetic nervous system in the progression of HF has been well documented and has been targeted at least in part by the clinical use of beta-adrenergic blockers (propranolol, carvidolol, metoprolol) or "beta-blockers" in this patient population. Although beta-blockers have decreased mortality and morbidity associated with HF, they have several limitations. Beta-blockers do not directly decrease sympathetic output since they only affect a sub-population of the receptors at which norepinephrine (NE), the major sympathetic neurotransmitter, acts. Other adrenergic receptors that are unaffected by beta blockade have been implicated in the myocardial pathogenesis associated with HF. For example, alpha1 receptors have been implicated in myocardial hypertrophy and fibroblast hyperplasia. Also, NE is not the only neurotransmitter contained in sympathetic neurons. Neuropeptides (somatostatin, neuropeptide Y) and other chemicals (adenosine, ATP) may also be released from sympathetic nerves and play significant but as of yet poorly understood roles in the pathophysiology of HF.

Sympatholytic cardiovascular agents, particularly, adrenergic stimulants (central) that decrease the sympathetic nerve output, as opposed to inhibiting only a subset of postsynaptic receptors, may be more effective than beta-blockers. A "centrally acting" sympatholytic cardiovascular agent is one that when administered by a conventional route, e.g., orally or by injection into the blood stream, is capable of crossing the blood-brain barrier and can produce effects on the central nervous system. Suitable centrally acting adrenergic stimulants include Aldoclor® (methyldopa and chlorothiazide sodium); Aldomet® (methyldopa); Aldomet® ester HCL (methyldopate HC1); Aldoril® (methyldopa and hydrochlorothiazide); Catapres® (clonidine HC1); Catapres®-TTS (clonidine); Clorpres® (clonidine hydrochloride and 25 chlorthalidone); Combipres® (clonidine hydrochloride and chlorthalidone); and Tenex® (guanfacine). Other centrally acting adrenergic stimulants include p-aminoclonidine guanabenz, lidamidine, tizanidine, moxonidine, xylazine, detomidine, medetomidine, and dexmedetomidine. It is also known that certain local anesthetics, e.g., lidocaine, bupivacaine, and ropivacaine, that when administered directly to a sympathetic nerve have a local effect on the neurons that function in a sympatholytic manner. However, these local anesthetics that can act as a sympatholytic cardiovascular agent are not centrally acting, in that they cannot cross the blood-brain barrier.

Clonidine, also known as 2-[(2,6-dichlorophenyl)amino]-2-imidazoline is well known as a potent anti-hypertensive cardiovascular agent. Bolus intravenous injections of clonidine HCl have produced decreased sympathetic outflow, increased vagal tone and sensitivity of the baroreceptor reflex, with peak effects occurring at 5–20 minutes. Reductions were observed in heart rate, left ventricular filling pressure (preload), mean systemic arterial pressure (afterload), mean pulmonary artery pressure and right atrial pressure. See Giles, T. D. et al, "Acute Effects of Intravenous Clonidine HCl in Congestive Heart Failure", *Circulation*, II, 62(4), October 1980. Oral administration of clonidine and its addition salts is asserted in U.S. Pat. No. 4,603,141 to be useful in the treatment of HF patients particularly to enhance exercise tolerance. The major side effects associated with oral or transdermal clonidine are sedation and dry mouth.

Clonidine and related compounds have other therapeutic uses than in the treatment of HF. Chronic pain is presently treated by intrathecal infusion of opioids (e.g., morphine, fentanyl, hydromorphone) through an intrathecal catheter from an implantable drug pump implanted in the patient's body or from an external drug pump worn externally by the patient. Recently, clonidine has also been approved for epidural infusion for the treatment of chronic pain (Duraclon®, Roxane Labs) and is typically administered in combination with opioids. Abnormally low blood pressure (hypotension) and bradycardia are reported as undesirable side effects accompanying intrathecal delivery of clonidine. Consequently, an effort is underway to develop a centrally acting alpha2-agonist causing less cardiovascular side effects, such as tizanidine.

Monitoring Cardiac State and Therapy Efficacy:

The efficacy (or lack of efficacy) of the cardiovascular agent or agents delivered in a prescribed drug regimen must be carefully monitored and periodically assessed by the treating physician through use of patient interviews and a variety of tests. Patient data relevant to the state of health of a HF patient includes the patient's current ability to exercise and perform daily activities and the patient's self assessments that are periodically completed as set forth in commonly assigned U.S. Pat. No. 6,280,409. The progression of the disease and the efficacy of prescribed drug regiments can be assessed by periodically accurately measuring heart geometry, the degree of heart enlargement, and the mechanical pumping capability of the heart, e.g., ejection fraction, under a variety of metabolic conditions the patient is likely to encounter on a daily basis and typically employing external echocardiogram equipment in the clinical setting. However, the measurement procedure is time consuming to perform for even a resting patient and cannot be practically performed replicating a range of metabolic conditions. Typically, the echocardiography procedure is performed infrequently and months or years may lapse between successive tests, resulting in a poor understanding of the progress of the disease or whether or not intervening drug regimens have been efficacious.

A number of implantable cardiac monitors have been proposed and certain ones are clinically available. For example, a patient activity monitor is disclosed in the above-referenced '409 patent for implantation in a HF patient to record patient activity, e.g., walking, over a period of time. It may be concluded that the drug regimen is efficacious if the activity record exhibits increasing activity level over time or is either not efficacious or is not being adhered to by the patient if the activity record does not exhibit increasing activity level over time.

A monitor/stimulator is disclosed in U.S. Pat. No. 5,417,717, that monitors and assesses level of cardiac function then permits a physician to arbitrate the therapy mode, if therapy is indicated. The monitor/stimulator assesses impedance, EGM, and/or pressure measurements, and then calculates various cardiac parameters. The results of these calculations determine the mode of therapy to be chosen. Therapy may be administered by the monitor/stimulator itself or a control signal may be telemetry transmitted to various peripheral devices aimed at enhancing the heart's function. Alternatively, the monitor/stimulator may be programmed to monitor and either store or telemeter information without delivering therapy.

An HF monitor/stimulator is disclosed in commonly assigned U.S. Pat. No. 6,104,949 that senses the trans-thoracic impedance as well as patient posture and provides a record of same to diagnose and assess the degree and progression of HF. The sensed trans-thoracic impedance is dependent on the blood or fluid content of the lungs and assists in the detection and quantification of pulmonary edema symptomatic of HF. Trans-thoracic impedance is affected by posture, i.e. whether the subject is lying down or standing up, and the sensed trans-thoracic impedance is correlated to the output of the patient posture detector to make a determination of presence of and the degree of pulmonary edema for therapy delivery and/or physiologic data storage decisions.

Implantable physiologic cardiac monitors for monitoring the mechanical and/or electrical heart function have been proposed and, in some cases, implemented for deriving and storing EGM and mechanical performance data over a prolonged time.

It has been proposed, as described in commonly assigned, co-pending U.S. patent application Ser. No. 10/002,338 filed Oct. 30, 2001, and Publication No. 2003/0100925 to employ various types of sensors including accelerometers, magnets, and sonomicrometers typically located in a blood vessel or heart chamber that respond to or move with mechanical heart function to derive a metric that changes in value over the heart cycle in proportion to the strength, velocity or range of motion of one or more of the heart chambers or valves. Such a mechanical function metric would complement the measurement of blood pressure and the EGM to more confidently determine the degree of change in the HF condition of the heart.

An implantable EGM monitor for recording the cardiac electrogram from electrodes remote from the heart as disclosed in commonly assigned U.S. Pat. No. 5,331,966 and PCT publication WO 98/02209 is embodied in the Medtronic® REVEAL® Insertable Loop Recorder having spaced housing EGM electrodes. More elaborate implantable hemodynamic monitors (IHMs) for recording the EGM from electrodes placed in or about the heart and other physiologic sensor derived signals, e.g., one or more of blood pressure, blood gases, temperature, electrical impedance of the heart and/or chest, and patient activity have also been proposed. In particular, the Medtronic® CHRONICLE® Implantable Hemodynamic Monitor (IHM) system comprises a CHRONICLE® Model 9520 IHM of the type described in commonly assigned U.S. Pat. No. 5,368,040 coupled with a Model 4328A pressure sensor lead that monitors the EGM of the heart and senses blood pressure within a heart chamber using a pressure sensing transducer of the type disclosed in commonly assigned U.S. Pat. No. 5,564,434. The CHRONICLE® Model 9520 IHM measures absolute blood pressure, and the patient is also provided with an externally worn Medtronic® Model No. 2955HF atmospheric pressure reference monitor of the type described in commonly assigned U.S. Pat. No. 5,810,735 to record contemporaneous atmospheric pressure values.

A further IHM is disclosed in commonly assigned U.S. Pat. No. 6,438,408 that measures a group of parameters indicative of the state of HF employing EGM signals, measures of blood pressure including absolute pressure P, developed pressure DP (DP=systolic P–diastolic P), and/or dP/dt, and measures of heart chamber volume (V) over one or more cardiac cycles. These parameters include: (1) relaxation or contraction time constant tau ($\tau$); (2) mechanical restitution (MR), i.e., the mechanical response of a heart chamber to premature stimuli applied to the heart chamber; (3) recirculation fraction (RF), i.e., the rate of decay of PESP effects over a series of heart cycles; and (4) end systolic elastance ($E_{ES}$), i.e., the ratios of end systolic blood pressure P to volume V. These HF state parameters are determined periodically regardless of patient posture and activity level. However, certain of the parameters are only measured or certain of the data are only stored when the patient heart rate is regular and within a normal sinus range between programmed lower and upper heart rates. The parameter data is associated with a date and time stamp and with other patient data, e.g., patient activity level, and the associated parameter data is stored in IMD memory for retrieval at a later date employing conventional telemetry systems. Incremental changes in the parameter data over time, taking any associated time of day and patient data into account, provide a measure of the degree of change in the HF condition of the heart.

Methods and apparatus for developing estimates of the ventricular afterload derived from ventricular pressure measurements employing the CHRONICLE® Model 9520 IHM coupled with a Model 4328A pressure sensor lead are described in commonly assigned, co-pending U.S. patent application Ser. No. 10/376,064 filed Feb. 26, 2003. The estimates of the ventricular afterload can be used to quantify the current state of cardiovascular function, to discern changes in the state of cardiovascular function over time, and to select or alter a therapy delivered by an IMD to optimize cardiovascular function of patients experiencing HF, hypertension, and other clinical pathologies A system and method are disclosed in commonly assigned co-pending U.S. patent application Ser. No. 10/368,278 filed Feb. 18, 2003, for detecting mechanical pulsus alternans (MPA) as well as associated electrical alternans and other MPA episode data from ventricular pressure and EGM measurements employing the CHRONICLE® Model 9520 IHM coupled with a Model 4328A pressure sensor lead. The collected MPA episode trend data provides indicia related to the mechanical performance of the HF patient's heart so that the response of the heart to drug or electrical stimulation therapies prescribed to reduce HF symptoms can be assessed.

It has also been proposed to detect ischemic conditions of the heart from EGM characteristics, particularly, ST segment elevation, and mechanical heart motion as measured by an accelerometer or changes in measured blood pressure, for example, as described in commonly assigned, co-pending U.S. Patent Application Publication Nos. US 2003/0045805 and US 2002/0120205.

Patient Worn and Implantable Drug Delivery Systems:

A variety of patient worn and implantable drug delivery systems have been developed that obviate the problems that arise from patient non-compliance with the prescribed drug regimen, that are convenient to use and enable more precise dosage titration, and that reduce side effects as a result of the dosage titration and because the drug can, in certain cases, be delivered to an optimal delivery site rather than being injected into the blood stream or ingested.

Implantable drug pumps having drug reservoirs that can be refilled through ports accessed transcutaneously and coupled with catheters extending from the reservoir to a delivery site have been developed or proposed to deliver a variety of drugs. The Medtronic® SynchroMed® Infusion System approved for certain clinical uses comprises an Implantable Infusion Pump (IIP) coupled to a catheter. The battery powered IIP can be advantageously programmed to frequently or continuously deliver drug boluses of drugs that have a short duration of activity directly to an efficacious site. The IIP is surgically implanted subcutaneously under the skin such that the refill port is directed outward. The IIP reservoir can be refilled as necessary. Adverse side effects are reduced and the mental and physical states of many patients are improved by the automatically administered drug therapy. It is not necessary to rely upon the patient to comply with the prescribed regimen.

The Medtronic® SynchroMed® Infusion System is approved for intrathecal drug delivery treatment of spasticity by intrathecal administration of baclofen and to reduce chronic pain by intraspinal administration of the opioids morphine and fentanyl. It has been proposed to deliver insulin into the central nervous system employing the Medtronic® SynchroMed® Infusion System in commonly assigned, co-pending U.S. patent application Ser. No. 10/133,251 filed Apr. 26, 2002. One end of the drug infusion catheter is connected to the IIP, and the other end of the catheter is threaded into a cerebral spinal fluid (CSF) filled sub-arachnoid, intrathecal space in the patient's spinal cord. An IIP comprising an implantable pump and catheter is disclosed in commonly assigned U.S. Pat. Nos. 5,643,207 and 5,782,798 for dispensing pancreatic polypeptide blockers and other drugs that decrease sensations of hunger and increase satiety into particular sites in the brain through a distal catheter segment that is implanted through the skull and extends to the specific sites.

Methods for administration of clonidine employing a Medtronic® SynchroMed® Infusion System to a human patient suffering from acute or chronic pain, most preferably neuropathic pain, are disclosed in commonly assigned U.S. Pat. No. 5,801,188. An increasing dosage of clonidine is administered throughout a treatment regimen, wherein the amount of clonidine administered intraspinally is gradually increased over the treatment period to minimize adverse hemodynamic side effects. In preferred embodiments, the drug is administered intrathecally or epidurally, most preferably intrathecally, in a dosage of up to about 1200 mcg/day of clonidine over a treatment period of about 4 to 12 weeks. The amount of clonidine administered is increased periodically, preferably between once and about three times per day. Clonidine administration is increased by about 0.5 to about 5 mcg/hr during the administration period, resulting in a clinically effective dose of from about 4 to 50 mcg/hr.

Multiple IMDs:

It has also been proposed to implant multiple IMDs in the same patient, and to enable communication between the IMDs, whereby the multiple IMDs function cooperatively as disclosed, for example, in the above-referenced '409 patent and in commonly assigned U.S. Pat. Nos. 4,987,897. The multiple IMDs include tissue stimulators, e.g., cardiac pacemakers, implantable cardioverter-defibrillators (ICDs), gastrointestinal stimulators, deep brain stimulators, and spinal cord stimulators, implantable drug pumps, and implantable physiologic and activity sensors.

It has been proposed in U.S. Pat. No. 5,330,505, for example, to combine the features of disparate IMDs, e.g., an implantable drug pump with a tissue or organ stimulator and with remote physiologic sensors, to provide multiple functions. In both cases, the IMD or IMDs communicate with external proximate medical devices, e.g., programmers and patient control units, and remote medical devices and systems employing a variety of data transmission techniques.

In commonly assigned U.S. Pat. No. 5,919,210, an IMD is disclosed that detects dysautonomic syncopes, e.g., vasovagal syncope, and endocardially infuses a drug in response thereto. A variety of sensors are placed in locations where the physiological activity to be detected is most prominent and more feasibly detected. Such sensors include, but are not limited to, those which can detect heart rate (R—R interval), atrio-ventricular interval (AVI), QT interval, QT/R—R ratio, heart rate variability indices such as HF, LF, LF/HF ratio, QRS or ventricular electrogram integral (area under depolarization signal), QRS duration, myocardial contractility index (accelerometer signal), subcutaneous blood flow mean value (SubQ BF), SubQ BF variability indices, motion, pH, temperature, position and chest wall impedance for monitoring respiration rate. The physiological activities used to determine the need for treatment include changes in heart rate, heart rate variability, QT interval, PR interval, pressure, blood flow, vagal nerve activity, temperature, pH, and AV conduction times, position, respiration rate and combinations thereof. The drug infusion catheter is placed according to the desired treatment regimen. For example, the drug infusion catheter may be placed within the coronary sinus, right atrium or right ventricle to provide rapid infusion with little dilution of pharmacological therapy.

A number of systems have been proposed to combine the delivery of an appropriate anti-arrhythmic drug therapy as an alternative or companion therapy with the delivery of an appropriate cardioversion/defibrillation shock as described, for example, in the above-referenced '897 patent and in U.S. Pat. Nos. 5,087,243 and 5,269,301. In these systems, an IIP is combined with an ICD, the system having a decision-making control algorithm to govern the diagnosis of the arrhythmia, prioritize the therapies to be delivered, and deliver the therapies. It is hoped that the delivered drug therapies can reduce the frequency of the need to deliver a cardioversion/defibrillation shock by either suppressing the tachyarrhythmia entirely or converting it to a lower rate or less chaotic tachyarrhythmia amenable to conversion by less aggressive high rate pacing therapies.

In commonly assigned U.S. Pat. No. 5,893,881, a method of and apparatus is disclosed for providing atrial cardioversion shocks to the atria of a patient's heart in need of cardioversion, wherein the application of the cardioversion shock to the atria follows the delivery of the pain alleviating therapy by time sufficient to allow the therapy to take effect. The pain alleviating therapies include intraspinal delivery of electrical stimulation or an analgesic drug bolus. The methodological sequence to provide the pain alleviating drug therapy to counter the pain induced by delivery of atrial cardioversion energy includes the initial detection of atrial fibrillation, optional warning to the patient, intraspinal drug infusion therapy to produce analgesia, time out to allow analgesia to take effect and the charge storage capacitors to be charged, re-verification of atrial fibrillation, delivery of the cardioversion energy, and verification that successful atrial defibrillation has taken place. Advantageously, the propagated pain induced by the delivery of cardioversion energy may be reduced, particularly in atrial cardioversion, to a level allowing greater patient comfort and acceptance of the cardioversion therapy, particularly atrial cardioversion.

Combined neurological stimulation and/or drug delivery and cardiac therapy delivery devices are disclosed in further commonly assigned co-pending U.S. Patent Application Publication Nos. US 2002/0165586, 2002/0143369, 2002/0107553, and 2003/0004549. Cardiac insult or anticipated cardiac insult is detected from monitored physiologic states, and electrical stimulation may be provided to peripheral nerves, intrinsic cardiac nerves, sympathetic ganglia, cranial nerves, and may generally be directed to the vertebral column, or within the chest wall of the patient. A drug delivery system optionally included in the system delivers biologically active agents based on the anticipation of the occurrence of the cardiac insult.

Despite the wide variety of IMDs and methods of treatment that have been proposed in the prior art, a need remains for an efficacious way of delivering drug therapies to patients in HF or suffering pathologies associated with HF.

BRIEF SUMMARY OF THE INVENTION

The present invention satisfies this need by detecting symptoms of pathologies associated with HF, and triggering delivery of a sympatholytic cardiovascular agent to a central nervous system site to alleviate such symptoms and otherwise treat HF and pathologies associated with HF.

The sympatholytic cardiovascular agent is preferably delivered to treat HF or pathologies associated with HF which include any disease process that involves over-activity of the sympathetic nervous system comprising the specific cardiovascular indications: angina, hypertension, coronary artery disease, and cardiac arrhythmias. In addition, the sympatholytic cardiovascular agent can be delivered to treat cardiovascular-related diseases in which the sympathetic nervous system is overactive, e.g., major depression and sleep apnea.

The sympatholytic cardiovascular agent is preferably delivered into the central nervous system accessed at one of: the sub-arachnoid space; the sub-arachnoid space of the spinal cord; the sub-arachnoid space of the thoracic spinal cord; the sub-arachnoid space between the first and fifth thoracic vertebrae; the sympathetic preganglionic cell bodies located in the intermediolateral cell column of the spinal cord; the preganglionic sympathetic neurons which provide innervation to the heart; and the preganglionic sympathetic neurons which provide innervation to the kidneys to prevent stimulation of the renin-angiotensin cascade.

In one embodiment, one end of an infusion or drug infusion catheter is threaded into the selected infusion site in the central nervous system, e.g., the sub-arachnoid, intrathecal space in the patient's spinal cord, and the other end of the drug infusion catheter is connected to an IIP implanted subcutaneously or is extended through the skin and coupled to an external drug pump.

The external drug pump or the IIP are preferably programmable by the treating physician to deliver a baseline bolus volume at a particular frequency of delivery (baseline dosage) at implantation and from time to time during patient work-ups. The competent patient can be instructed to operate the external drug pump or can be provided with an external, hand-held, patient-controlled, activator or "patient activator" that can communicate with the IIP. In either case, the patient can operate the external drug pump or the patient activator to provide additional boluses of the sympatholytic cardiovascular agent, within prescribed frequency and dosage limits, in order to pre-empt increases in blood pressure associated with physical exercise, stress, or other events associated with increases of blood pressure. For example, the patient may command delivery of an additional bolus after measuring blood pressure using standard noninvasive methods and determining that blood pressure is too high.

In other embodiments, an IHM coupled with at least one sensor detects physiologic parameters associated with HF or pathologies associated with HF and triggers delivery by a drug delivery device of a sympatholytic cardiovascular agent to a central nervous system site to alleviate such symptoms and otherwise treat HF. Preferably, the drug delivery device is an external drug pump or an IIP coupled in either case with a catheter extending to a selected delivery site of the central nervous system. The IIP and IHM can be combined into a single IMD or can constitute separate IMDs that communicate by any of the known communication mechanisms.

The physiologic sensor(s) of the IHM preferably comprise one or more of an EGM sensor, a patient activity sensor, a cardiac mechanical function metric determining sensor, a blood chemistry sensor, an arterial, venous or heart chamber blood pressure sensor, a blood temperature sensor, a neural activity sensor, and a molecular probe. The EGM signal can be processed to determine one or more of heart rate, heart rate variability, and aberrations in the PQRST segment include changes in morphology, ST segment elevation, electrical alternans, and interval changes associated with HF or a pathology associated with HF.

In other embodiments, the IHM incorporates EGM sense electrodes and a blood pressure sensor, which would typically be located on an electrical medical lead extending between the monitor housing and a site of measurement within the lumen of an artery or within a chamber of the heart or near or around the adventitial surface of an artery. The IHM preferably further includes a patient activity sensor.

The IHM and the external drug pump or IIP include operating systems that enable communication between them and with an external programmer and/or other external medical devices. The IIP operating system receives and stores communicated dosage commands that establish the dosage frequency and bolus volume of the sympatholytic cardiovascular agent. The IHM operating system processes the sensor output signal(s) and performs a dosage algorithm that determines an appropriate dosage (frequency and bolus volume) of the sympatholytic cardiovascular agent from the sensor output signal(s). The IHM operating system communicates the resulting dosage command to the IIP operating system where it is stored in IIP memory for use until the next dosage command is received. The IHM operating system also stores archival data in memory including time and date stamped sensor output signal and commanded dosage data for future interrogation by a physician employing an external programmer.

A baseline dosage correlated to a baseline physiologic sensor output signal is programmed by the physician at implantation and from time to time during patient work-ups. The baseline dosage frequency of delivery may be intermittent at specified intervals or continuous. A dosage adjustment from baseline dosage, e.g., a dosage adjustment in bolus volume or frequency of delivery, takes place as a function of the difference between a currently measured physiologic sensor output signal and the baseline physiologic sensor output signal. A weighting or scale factor can be programmed by the physician into the IHM memory to adjust the function. A maximum dosage adjustment (positive and negative) from baseline dosage may also be programmed by the physician.

The sympatholytic cardiovascular agent is one of the group consisting of an alpha-adrenergic agonist and an alpha2-adrenergic agonist, e.g., clonidine, p-aminoclonidine, guanabenz, lidamidine, tizanidine, moxonidine, methyldopa, xylazine, guanfacine, detomidine, medetomidine, dexmedetomidine, and a local anesthetic, e.g., lidocaine, bupivacaine, and ropivacaine.

In one example, clonidine may be delivered from the IIP into the central nervous system by continuous intrathecal infusion at a dosage of 0.01 to 1.0 mg/day or by continuous intrathecal infusion at a dosage of 50 to 500 mcg/day or by continuous intrathecal infusion at a dosage of 100 to 400 mcg/day. The clonidine formulation may comprise clonidine hydrochloride at a concentration of 0.5 to 10 mg/mL in a vehicle (solvent) comprising sterile water or 0.9% sodium chloride solution that is preferably free of preservatives and has a tonicity of 300±50 mOsm/L.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

The foregoing and other advantages and features of the present invention will be more readily understood from the following detailed description of the embodiments thereof, when considered in conjunction with the drawings, in which like reference numerals indicate identical structures throughout the several views, and wherein:

FIG. 4 is a simplified flow chart of the steps of operation of the external drug pump of FIGS. 1 and 3;

FIG. 5 is a simplified flow chart of the steps of operation of the IHM of FIG. 3;

DETAILED DESCRIPTION OF THE ILLUSTRATED EMBODIMENTS

In the following detailed description, references are made to illustrative embodiments for carrying out the invention. It is understood that other embodiments may be utilized without departing from the scope of the invention. For convenience, the functions and structures of the IIP and the IHM shall be described herein in the context of separate IMDs unless otherwise indicated when the functions and structures of the IIP and the IHM are incorporated into a single IMD. It will also be understood that the description of the functions of the IIP relate to a drug dispenser and a catheter extending to the site of drug delivery in the central nervous system. The drug dispenser may be fully implanted in the patient's body or may be worn externally on the patient's body.

Figure 1:
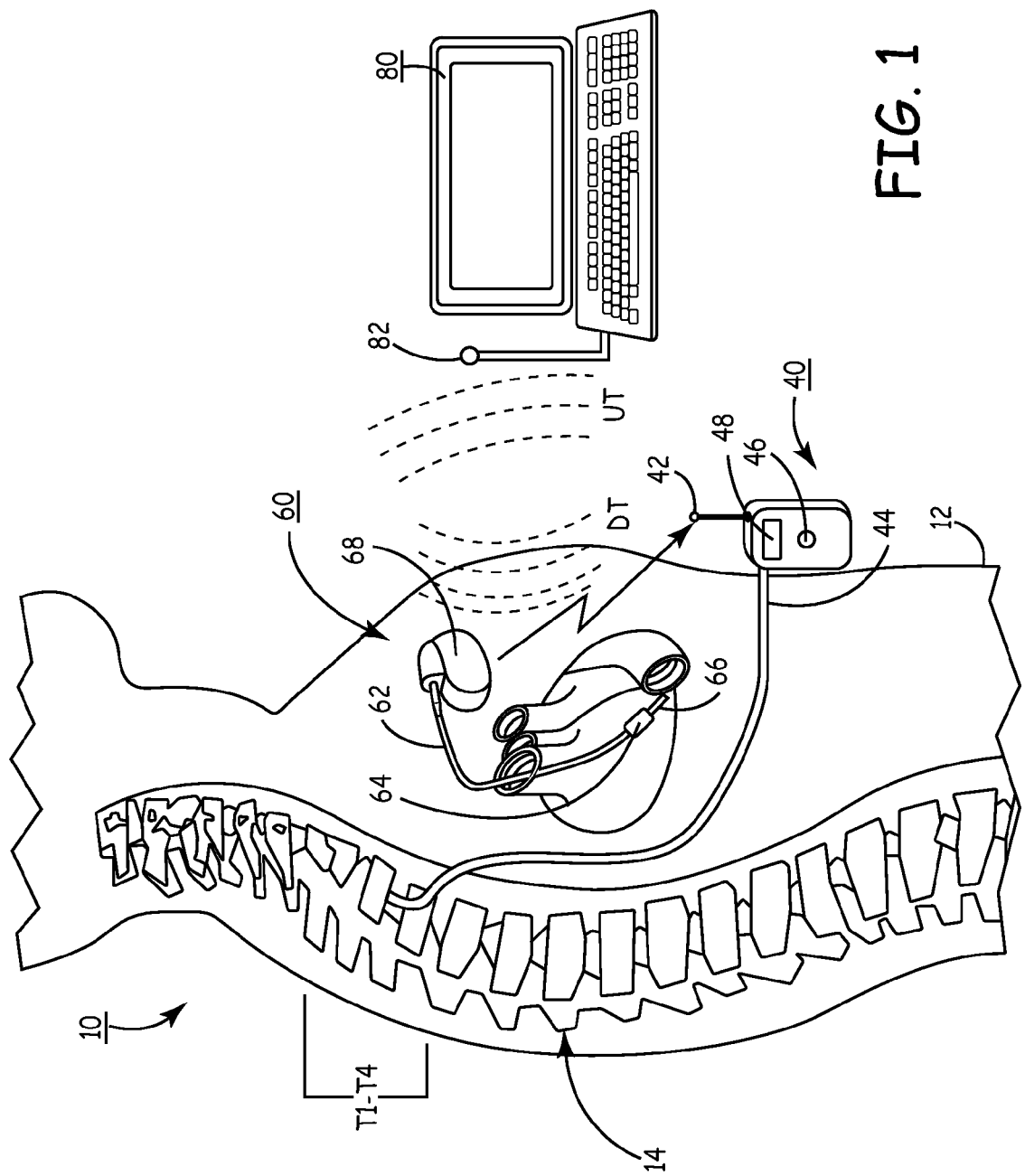
FIG. 1 is an illustration of a first exemplary, simple, patient-activated system in which the present invention can be implemented comprising an external drug delivery system carried by the patient optionally communicating with an IHM implanted in the patient.

Thus, in a first embodiment illustrated in FIG. 1, the present invention may be practiced employing an external drug pump 40 carried by patient 10. The distal end of an infusion or drug infusion catheter 44 is threaded into the selected infusion site in the central nervous system, e.g., the sub-arachnoid, intrathecal space in the patient's spinal cord 14, and the other end of the drug infusion catheter 44 is extended through the patient's skin and coupled to an output of the external drug pump 40.

External drug pump 40 used to deliver the sympatholytic agent into the CNS may comprise any of a number of external drug pumps that are available. Examples include ambulatory syringe pumps such as the CADD® Micro Ambulatory Infusion Pump manufactured by SIMS Deltec Inc. (St. Paul, Minn.), the MiniMed® Model 407C pump manufactured by Medtronic, Inc. (Northridge, Calif.), and the Panomat® C-10 manufactured by Disetronic, Inc. (St. Paul, Minn.). Another type of external pump that may be used is designed to work with a cassette or collapsible IV bag that serves as the drug reservoir. An example of this type of pump is the ambIT pump manufactured by Sorenson, inc. (West Jordan, Utah). These external drug pumps are able to accurately dispense small volumes of drug solution over extended periods of time, can be programmed by the physician, patient, or both, and can be easily refilled by replacing the syringe, cassette or bag. External pumps are typically attached to a connecting tube that extends through the patient's skin 12 and is tunneled subcutaneously to the posterior lumbar region where it is connected to the intrathecal infusion catheter 44. Examples of intrathecal infusion catheters 44 include the InDura® Models 8709 and 8711 infusion catheters manufactured by Medtronic, Inc.

A baseline dosage is programmed to be delivered by the external drug pump 40 at implantation of the drug infusion catheter 44 and during periodically scheduled patient workups. The baseline dosage frequency of delivery may be intermittent at specified intervals or continuous. The external drug pump 40 has an indicator, e.g., a display screen 48, which provides an indication of how much drug is left in the drug reservoir or other suitable information.

The patient may also be provided with the ability to operate the external drug pump 40 by depressing button 46 provide additional boluses of the sympatholytic cardiovascular agent, within prescribed frequency and dosage limits, in order to pre-empt increases in blood pressure associated with physical exercise, stress, or other events associated with increases of blood pressure. For example, the patient may initiate delivery of an additional dosage after measuring blood pressure using standard noninvasive methods and determining that blood pressure is too high. The physician may optionally disable this patient activation feature.

Figure 2:
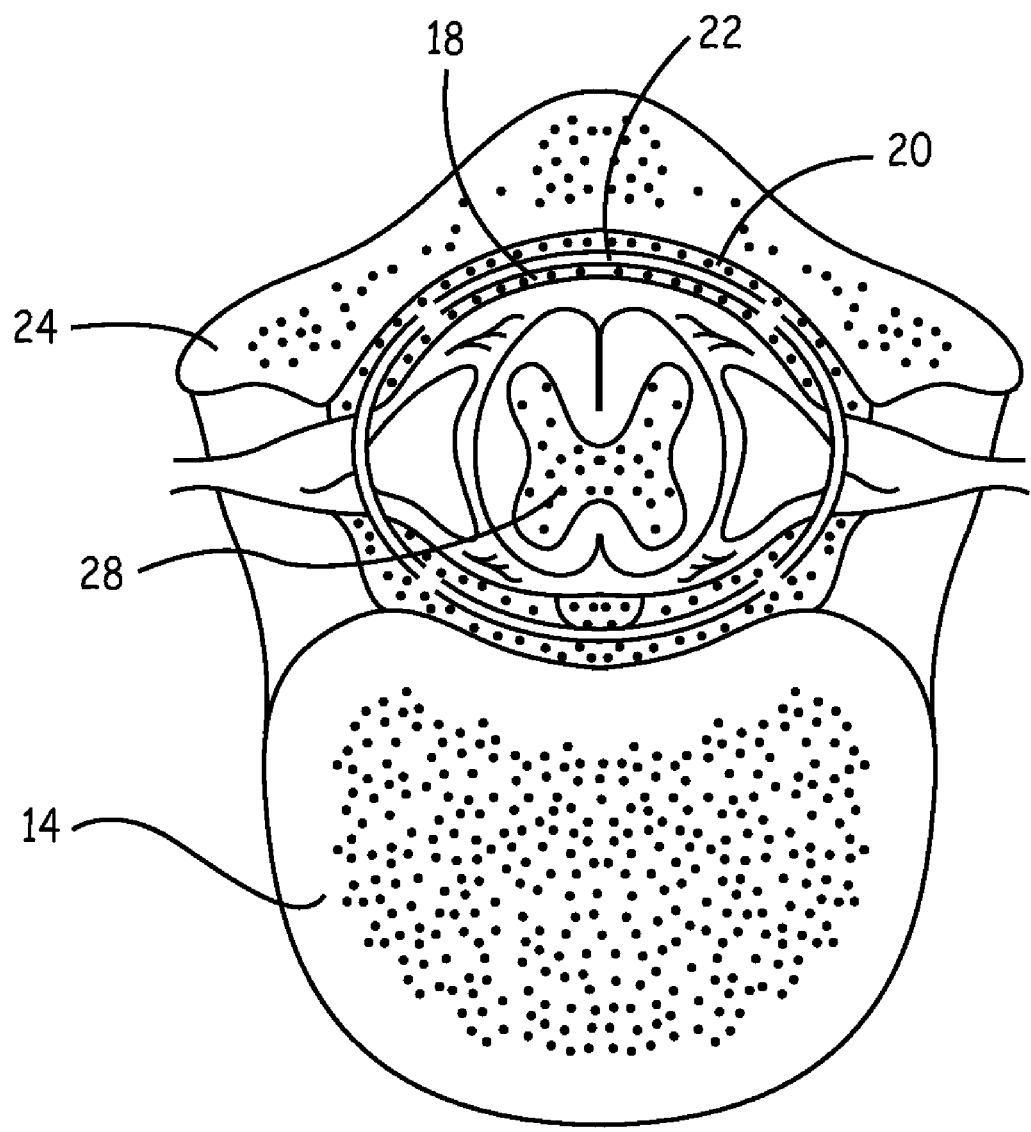
FIG. 2 is a cross-section view of the spinal column depicting the preferred sub-arachnoid, intrathecal site of delivery of the sympatholytic cardiovascular agent to alleviate symptoms and otherwise treat HF and pathologies associated with HF.

FIG. 2 is a cross-sectional view of the spinal column 14 of the body 10 that shows some potential infusion sites for location of the distal end of the drug infusion catheter 44. The spinal cord 28 is surrounded by three meningeal sheaths, which are continuous with those that encapsulate the brain, and is enclosed within the vertebral canal by the bones of the vertebrae 24. The dura matter 20 is the outermost of these three meningeal sheaths and is a dense, fibrous membrane. A subdural space within the dura matter 20 surrounds the arachnoid membrane 22, the second of the three meningeal sheaths that surround the spinal cord 28. The arachnoid membrane 22 is separated from the third meningeal sheath, the pia mater, by the sub-arachnoid or intrathecal space 18 that is filled with CSF.

The drug infusion catheter 44 is tunneled subcutaneously from the site of passage through the skin 12 (or connection with an IIP as described below) with a distal portion thereof extending between vertebrae 24. The distal end of the drug infusion catheter 44, including the distal end opening(s) of the catheter lumen, is passed through the arachnoid membrane 22. The intrathecal space is generally wide enough to accommodate a small catheter, thereby enabling chronic drug delivery systems. The catheter distal tip is thereby lodged in a selected sub-arachnoid intrathecal space 18 to infuse the dosage of the sympatholytic cardiovascular agent into the CSF therein to alleviate symptoms and otherwise treat HF and pathologies associated with HF. Such sub-arachnoid, intrathecal administration permits delivery of an effective dose that is only a fraction of the effective dose required by oral or parenteral administration.

Thus, the sympatholytic cardiovascular agent is delivered into the central nervous system accessed at one of: the sub-arachnoid space; the sub-arachnoid space of the spinal cord; the sub-arachnoid space of the thoracic spinal cord; the sub-arachnoid space between the first and fifth thoracic vertebrae; the sympathetic preganglionic cell bodies located in the intermediolateral cell column of the spinal cord; the preganglionic sympathetic neurons which provide innervation to the heart; and the preganglionic sympathetic neurons which provide innervation to the kidneys to prevent stimulation of the renin-angiotensin cascade.

Figure 6:
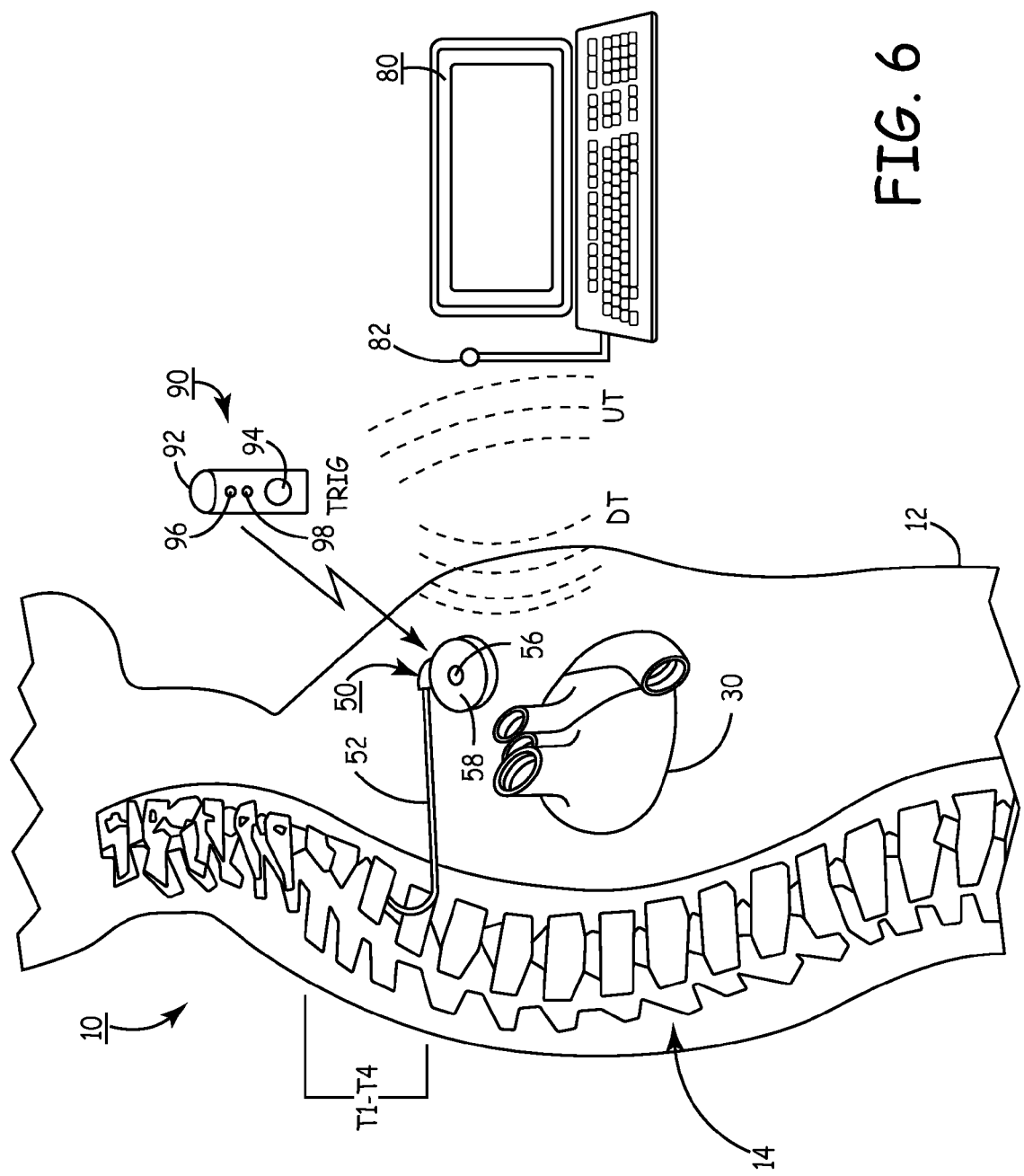
FIG. 6 is an illustration of a further exemplary, simple, patient-activated system in which the present invention can be implemented comprising an IIP implanted in the patient communicating with an external programmer and optionally communicating with a patient activator operated by the patient.
Figure 8:
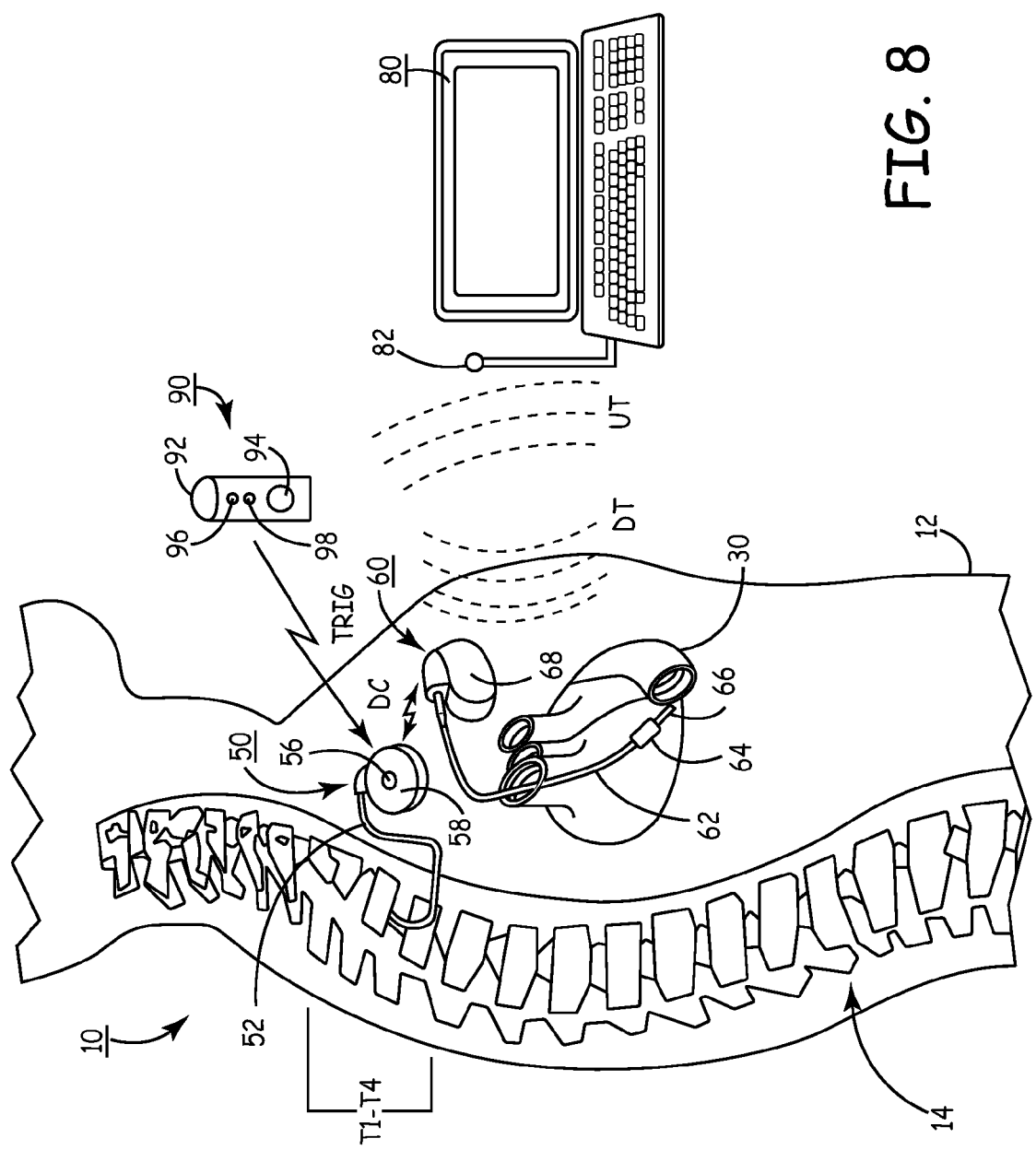
FIG. 8 is an illustration of a further exemplary system in which the present invention can be implemented comprising an IIP communicating with an IHM implanted in the patient and an external programmer and optionally communicating with a patient activator operated by the patient.
Figure 10:
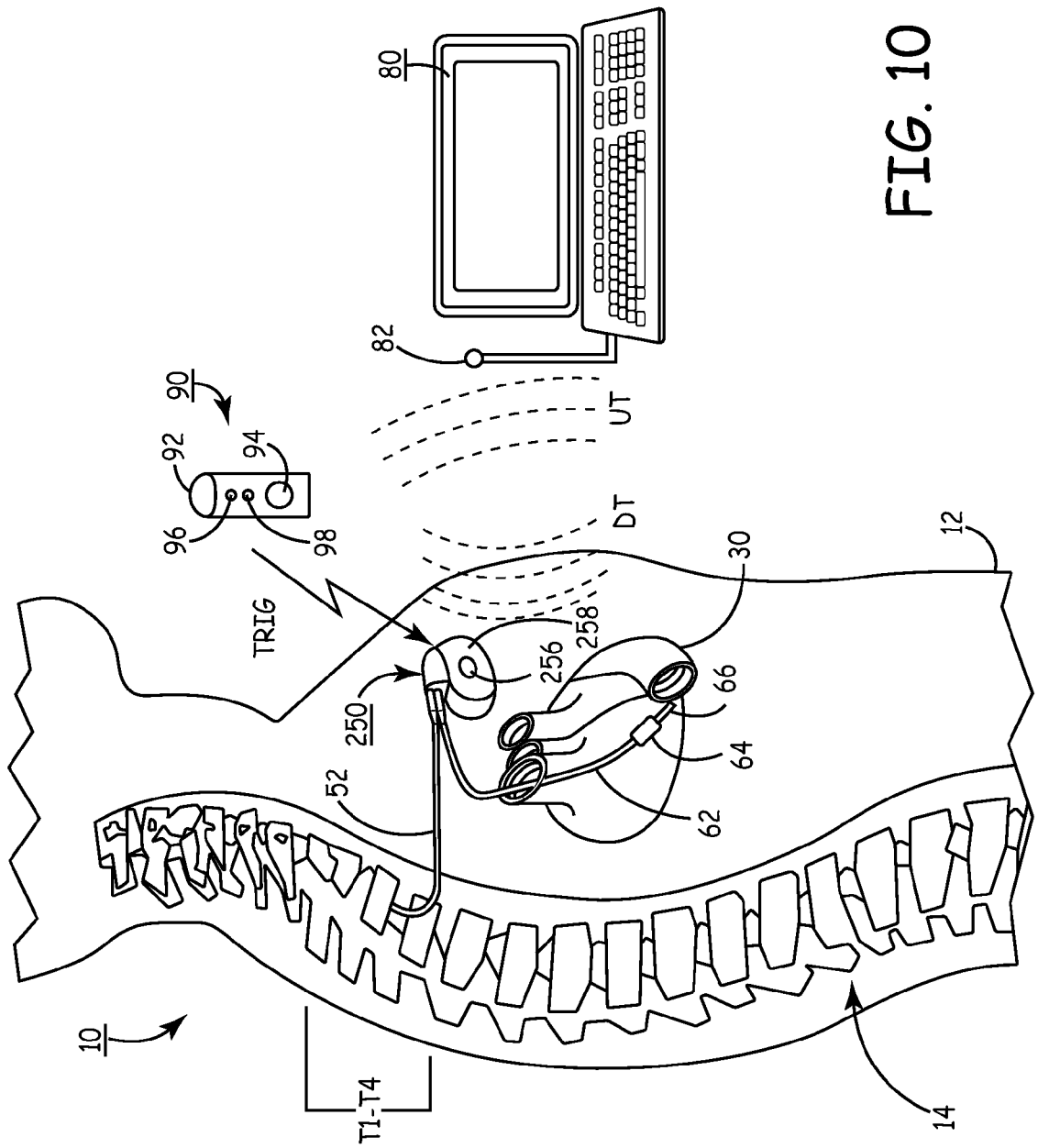
FIG. 10 is an illustration of a further exemplary system in which the present invention can be implemented comprising a combined IHM and IIP implanted in the patient communicating with an external programmer and optionally communicating with a patient activator operated by the patient.

The illustrated site of delivery in the region T1–T4 or T1–T5 is schematically depicted in FIG. 1 (also in FIGS. 6, 8 and 10). It will be understood that in practice the infusion catheter 44 is typically surgically introduced into the sub-arachnoid, intrathecal space in the lumbar region of the vertebrae between L1 and L4 and threaded upward within the subarachnoid, intrathecal space to about the level of T1–T4 so that the sympatholytic agent is delivered at the selected site of the central nervous system.

Referring again to FIG. 1, the external drug pump 40 may also be provided with the capability of communicating with an IHM 60 implanted within the patient's body 10 comprising a monitor housing 68 and an electrical medical lead 62. The sensors employed by the IHM 60 in all of the preferred embodiments, including the combined IHM and IIP 250 of FIGS. 10–12, can be selected to detect a wide variety of symptoms of HF and pathologies associated with HF as defined herein. The IHM operating system can process the sensor output signal(s) to assess the need for and trigger delivery of the sympatholytic cardiovascular agent into the central nervous system and assess the degree to which the heart responds to the delivery.

The sensors can include EGM sense electrodes coupled to EGM signal processing circuitry that derive heart rate and indices of aberrations in the shape of the PQRST segment that are symptomatic of HF or pathologies associated with HF. Heart rate variability can be determined, if present, from sequences of heart rate measurements. The aberrations in the PQRST segment include changes in morphology (e.g., the morphologies of the QRS wave and T-wave), ST segment elevation, electrical alternans (including T-wave alternans, QRS alternans, and ST segment alternans), and interval changes (including AV interval, QT interval).

Other suitable physiologic sensors that can be disposed in or about the heart 30 or elsewhere in the patient's body 10 include a patient activity sensor, one or more mechanical function metric determining sensor, one or more blood chemistry sensor, one or more arterial, venous or heart chamber blood pressure sensor and/or blood temperature sensor, neural activity sensors, molecular probes, and other sensors as described above. A plurality of physiologic sensors can be employed with the sensor output signals compared to thresholds set for each sensor and/or summed to derive an indicia of HF or a pathology associated with HF as defined herein. The aberrations in the PQRST segment and heart rate can be correlated to physiologic signals derived from the physiologic sensor(s) derive an indicia of HF or a pathology associated with HF.

The mechanical function metric determining sensors include one or more accelerometer or spaced apart magnets or sonomicrometers or impedance sense electrodes that are typically located in one or more cardiac vessel or heart chamber or heart wall location that respond to or move with mechanical heart function to derive a mechanical function metric that changes in value over the heart cycle in proportion to the strength, velocity or range of motion of one or more of the heart chambers or valves. Such mechanical function metric determining sensors can develop sensor output signals that reflect the degree of enlargement of the heart and the loss of contractility associated with HF, for example, and the degree to which the heart responds mechanically to the delivery of the sympatholytic cardiovascular agent into the central nervous system.

The blood chemistry determining sensors include one or more $PO_2$ sensor, $SAO_2$ sensor, glucose sensor, lactate sensor, $PCO_2$ sensor, pH sensor, and molecular probe. Certain molecular probes can assess indicators of myocardial ischemia, including troponin and CKMB. Other molecular probes that measure electrolytes, drug levels, catecholamines, rennin, angiotension, endogenous opiates and the like can be used to assess myocardial electrical instability, cardiac injury, or autonomic activity or tone. Pairs of blood chemistry sensors can be implanted in the patient's body to determine differences between the measured blood chemistry between the central arterial system and a peripheral artery that are indicative of a HF state or pathology associated with HF as defined herein.

The neural activity sensors can include one or more sensor disposed about the patient's body to detect one or more of cortical motor EEG, paraspinal muscle EMG, sympathetic nerve activity, parasympathetic nerve activity, and somatic nerve activity.

In this example depicted in FIG. 1, the electrical medical lead 62 is a cardiac lead supporting a physiologic sensor 64 comprising one or more of the physiologic sensors described above. The cardiac lead 62 also incorporates a distal EGM sense electrode 66 and a conventional fixation mechanism that fixes the sense electrode 66 in the ventricular apex in a manner well known in the art. The EGM is sensed between the active distal tip electrode 66 and the indifferent electrode formed by the hermetically sealed housing 68 in a conventional unipolar sensing configuration. Moreover, the IHM 60 preferably incorporates a patient activity sensor for determining the extent of exertion of the patient.

It will be understood that the IHM 60 can include additional electrical medical leads extending from the monitor housing 68 to a site of measurement disposing additional physiologic sensors and EGM electrodes within the lumen of an artery or within a chamber of the heart 30 or near or around the adventitial surface of an artery or nerve or elsewhere in the body. It will also be understood that other possible configurations of the IHM 60 can provide pacing therapies requiring additional implantable cardiac leads and sensing and pacing electrodes preferably for synchronously pacing upper and lower and right and left heart chambers for improving cardiac output in patients suffering from HF and provide cardioversion/defibrillation (C/D) therapies through additional C/D electrodes disposed about heart 30.

It will also be understood as described further below that the IHM 60 communicates with an external programmer 80 via an RF telemetry transmission scheme known in the art wherein digitally encoded RF signals are transmitted and received between the external programmer antenna 82 and the RF telemetry antenna of the IHM 60. Data accumulated in memory of IHM 60 can be uplink telemetry (UT) transmitted from the IHM 60 to the programmer 80 for display and analysis using the programmer 80 and for transmission onto a remote site over a suitable transmission link in a manner well known in the art. Similarly, interrogation and operating parameter commands formulated in the programmer 80 can be downlink telemetry (DT) transmitted from the programmer 80 to the IHM 60 in a manner well known in the art.

Communication between the external drug pump 40 and the IHM 60 can be effected via an RF telemetry transmission scheme known in the art wherein digitally encoded RF signals are transmitted and received between the external drug pump RF telemetry antenna 42 and the RF telemetry antenna of the IHM 60. In this variation of this embodiment of the invention, the operating system of the external drug pump 40 receives and stores dosage commands transmitted from the IHM 60 that establish the frequency of delivery and/or bolus volume of the dosage of the sympatholytic cardiovascular agent delivered through the drug infusion catheter 44. The IHM operating system processes the sensor output signal(s) and performs a dosage algorithm that determines an appropriate dosage (frequency and bolus volume) of the sympatholytic cardiovascular agent from the sensor output signal(s). The IHM operating system communicates the resulting dosage command to the operating system of the external drug pump 40 where it is stored in memory for use until the next dosage command is received. The IHM operating system also stores archival data in memory including time and date stamped sensor output signal and commanded dosage data for future interrogation by a physician employing the external programmer 80.

A baseline dosage correlated to a baseline physiologic sensor output signal (or weighted signals) is programmed by the physician employing programmer 80 at implantation and from time to time during patient work-ups. The baseline dosage frequency of delivery may be intermittent at specified intervals or continuous or be zero dosage. A dosage adjustment from baseline (dosage frequency and/or bolus volume) takes place as a function of the difference between a currently measured physiologic sensor output signal and the baseline physiologic sensor output signal. A weighting or scale factor that can be programmed by the physician into the IHM memory to adjust the function. A maximum dosage adjustment (positive and negative) from baseline dosage may also be programmed by the physician. The adjusted dosage is delivered between dosage adjustments.

The IHM 60 can include the operative features of the above-referenced Medtronic® CHRONICLE® Model 9520 IHM having the capabilities of deriving and storing the above-described blood pressure data as well as heart rate and other EGM data from the sensed ventricular EGM and deriving patient activity level as monitored by an activity sensor. The electrical medical lead 62 preferably comprises the above-referenced Model 4328A pressure sensor lead that senses blood pressure using a pressure sensing transducer of the type disclosed in the above-referenced commonly assigned '434 patent as physiologic sensor 64. As noted above, the CHRONICLE® Model 9520 IHM measures absolute blood pressure, and the patient is also provided with an externally worn Medtronic® Model No. 2955HF atmospheric pressure reference monitor to record contemporaneous atmospheric pressure values. It may not be necessary to employ such an atmospheric pressure reference monitor to adjust drug delivery dosage in the practice of the present invention.

The CHRONICLE® Model 9520 IHM can be programmed to measure the RV systolic pressure (maximum pressure in a sampling window), RV diastolic pressure (first sample in a sample window), pulse pressure (RV systolic–RV diastolic pressure), pre-ejection interval (PEI), systolic time interval (STI), peak positive and negative dP/dt, estimated pulmonary artery diastolic pressure (ePAD), patient activity level, and heart rate. As noted above, various other indices of cardiac function including ST segment elevation and measures of afterload can be derived from the measured EGM and pressure parameters.

The pressure parameters are sampled at a sampling rate of 256 samples per second, digitized and stored in memory registers. The samples are taken in a sampling window of each heart cycle of 20 ms through 500 ms following the detection of an R-wave, unless the R-wave occurs earlier. The Model 9520 IHM is programmed and interrogated employing an external Model 9790 programmer or a PC with CHRONICLE® software to accumulate trend data stored in a large FIFO buffer in RAM at a programmable resolution. The buffer can be filled in approximately an hour using the highest resolution or in about two months using the lowest resolution.

The memory buffers of the CHRONICLE® Model 9520 IHM and the externally worn Medtronic® Model No. 2955HF atmospheric pressure reference monitor can be interrogated to telemetry transmit the measured and stored pressure and other data, thereby emptying the buffers, to a nearby Model 9521 HF Interactive Remote Monitor for temporary storage of the data. The Model 9521 HF Interactive Remote Monitor external medical device periodically transmits accumulated data to a remote data processing center that processes the data to develop trend data that the attending physician can review with other patient data derived in patient examinations and interviews to assess the HF state.

Figure 3:
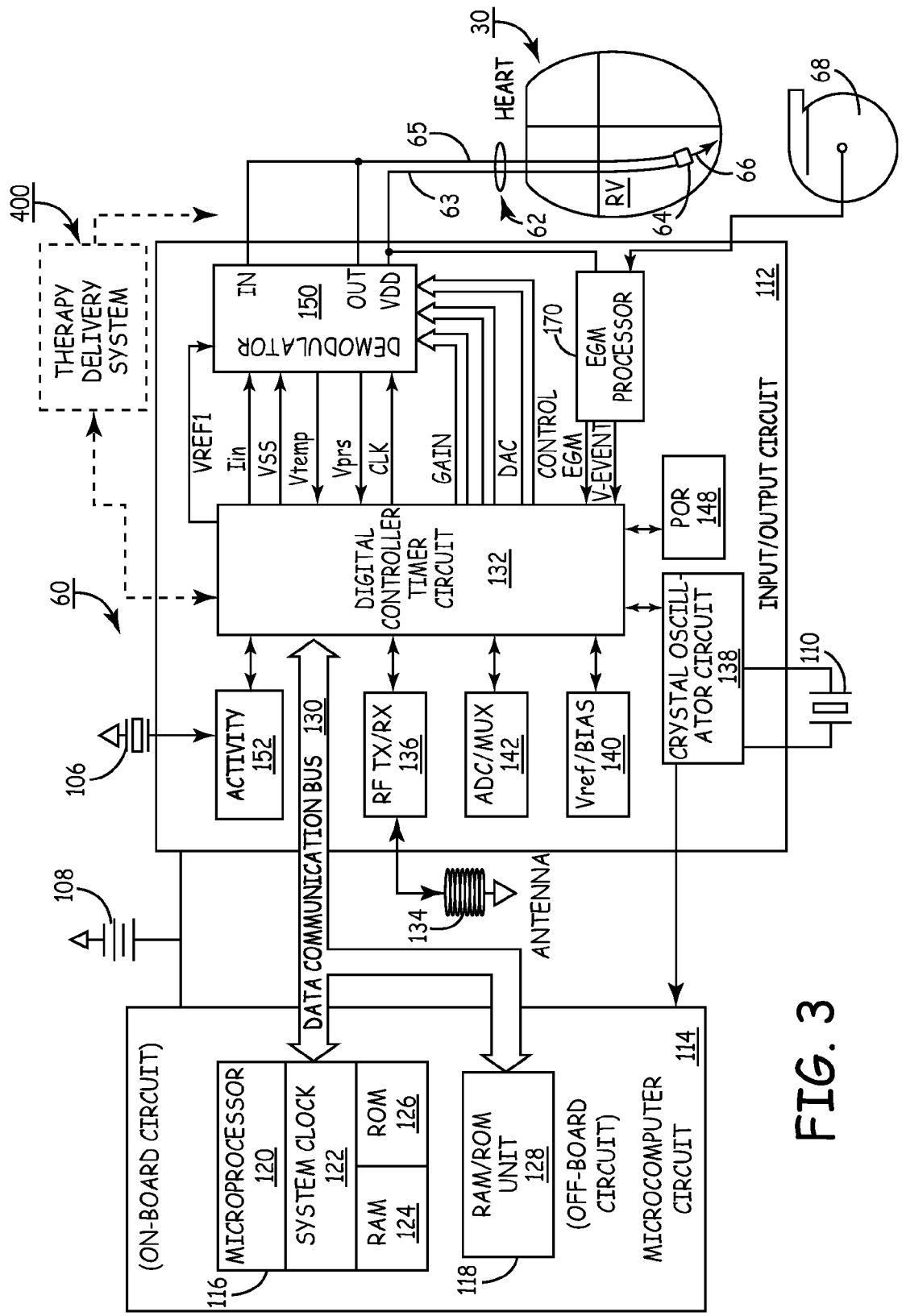
FIG. 3 is a simplified block diagram of one embodiment of IHM circuitry and associated lead(s) extending into the patient's heart and optionally employed in the system of FIG. 1 to monitor patient activity and/or cardiac function and provide one or more sensor output signal employed in one aspect of the present invention.

One example of an operating system of IHM 60 coupled with the cardiac lead 62 is depicted schematically in FIG. 3.

The IHM 60 obtains digitized EGM samples, digitized blood pressure and temperature measurements derived from absolute pressure and temperature sensor 64, and measurements of patient activity. The IHM operating system performs the dosage algorithm to formulate the dosage command that is communicated to the external drug dispenser 40.

The circuitry of the IHM operating system is powered by battery 108 and generally comprises a microcomputer 114 coupled through data communication bus 130 with an input/output circuit 112. The input/output circuit 112 is also coupled to an activity sensor 106, a telemetry antenna 134, a battery 108, and a crystal 110. The IHM 60 can be configured as a therapy delivery device by inclusion of a therapy delivery system 400 of the types described above shown in broken lines. The input/output circuit 112 includes a digital controller/timer circuit 132 and the associated components including a crystal oscillator 138, power-on-reset (POR) circuit 148, Vref/BIAS circuit 140, ADC/MUX circuit 142, RF transceiver circuit 136, activity circuit 152, pressure signal demodulator 150, and EGM sense amplifier 170. Crystal oscillator circuit 138 and crystal 110 provide the basic timing clock for the digital controller/timer circuit 132 and circadian or real time clock 134. Vref/BIAS circuit 140 generates stable voltage reference Vref and current levels from battery 108 for the circuits within the digital controller/timer circuit 132, and the other identified circuits including microcomputer 114 and demodulator 150. Power-on-reset circuit 148 responds to initial connection of the circuitry to the battery 108 for defining an initial operating condition and also resets the operating condition in response to detection of a low battery voltage condition. Analog-to-digital converter (ADC) and multiplexor (ADC/MUX) circuit 142 digitizes analog signals Vprs and Vtemp received by digital controller/timer circuit 132 from demodulator 150 for processing within microcomputer 114. ADC/MUX circuit 142 also multiplexes the data transmitted out through RF transceiver circuit 136 during UT transmission to programmer 80. Voltage reference and bias circuit 140, ADC/MUX circuit 142, POR circuit 148, crystal oscillator circuit 138 and optional activity circuit 152 may correspond to any of those presently used in currently marketed IHMs and cardiac pacemaker IPGs.

The digital controller/timer circuit 132 includes a set of timers and associated logic circuits connected with the microcomputer 114 through the data communications bus 130. Microcomputer 114 contains an on-board chip including microprocessor 120, associated system clock 122, and on-board RAM and ROM chips 124 and 126, respectively. In addition, microcomputer 114 includes an off-board circuit 118 including separate RAM/ROM chip 128 to provide additional memory capacity. Microprocessor 120 is interrupt driven, operating in a reduced power consumption mode normally, and awakened in response to defined interrupt events, which may include the periodic timing out of data sampling intervals for storage of monitored data, the transfer of triggering and data signals on the bus 130 and the receipt of programming signals. A real-time clock and calendar function may also be included to correlate stored data to time and date. Microcomputer 114 controls the operating functions of digital controller/timer 132, specifying which timing intervals are employed, and controlling the duration of the various timing intervals, via the bus 130.

An RF transceiver 136 coupled to RF telemetry antenna 134 serves both to demodulate received DT transmissions from the external programmer 80 of FIG. 1 and to UT transmit data to the external programmer 80 and to communicate dosage commands to the external drug dispenser 40. DT transmitted parameter values and operating modes are received through the RF telemetry antenna 134, demodulated in the RF transceiver circuit 136, and stored in RAM/ROM chip 128. Calculated dosage commands are transmitted by RF transceiver 136 through RF telemetry antenna 134 to the RF telemetry antenna 42 of the external drug dispenser 40 of FIG. 1.

The cardiac lead 62 shown in FIG. 3 comprises a pair of electrical conductors 63 and 65 extending through an insulating lead body to the distal pressure and temperature sensor 64 and distal sense electrode 66 within the right ventricle (RV) of heart 30. The EGM is sensed between the active distal tip electrode 66 and the indifferent electrode formed by the hermetically sealed monitor housing 68 in a conventional unipolar sensing configuration. The EGM signal processor 170 outputs digitized samples of the PQRST complex, and also includes a sense amplifier stage that declares a V-EVENT when the R-wave is sensed. The V-EVENT supplied to the digital controller/timer circuit 132 and functions as an interrupt to the microprocessor 120 in a manner well known in the art. The EGM signal samples are also processed to derive other indicia of HF or pathologies associated with HF.

A number of power, timing and control signals described in greater detail in the above-incorporated, commonly assigned, '434 and '752 patents are supplied by the digital controller/timer circuit 132 to the demodulator 150 to initiate and power the operation of the blood pressure sensor 64 and selectively read out the pressure and temperature signals Vprs and Vtemp. The active lead conductor 65 is attached through the connector block terminals to input and output terminals of demodulator 150 that supplies a voltage VREG at the output terminal. The passive lead conductor 63 is coupled through to the VDD supply terminal of the demodulator 150. The voltage signals Vprs and Vtemp, developed from intervals between current pulses received at the input terminal, are provided by demodulator 150 to the digital controller/timer circuit 132. The voltage signals Vprs and Vtemp are digitized in an ADC/MUX circuit 142 and stored temporarily in RAM/ROM chip 128 in a manner well known in the art for processing in accordance with the present invention.

As noted above, the IHM operating system processes the sensor output signal(s) and performs a dosage algorithm retained in memory in microcomputer 114 that determines an appropriate adjusted dosage (frequency and bolus volume) of the sympatholytic cardiovascular agent from the sensor output signal(s). The IHM operating system communicates the resulting dosage command to the drug dispenser operating system of drug dispenser 40 of FIG. 1. The dosage command received by external drug dispenser 40 is stored in memory for use until the next dosage command is transmitted from IHM 60 and received by the drug dispenser. The IHM operating system also stores archival data in memory including time and date stamped sensor output signal and commanded dosage data for future interrogation by a physician employing the external programmer 80.

The general operation of a drug delivery system, including the external drug dispenser 40 (and the IIP described further below) is set forth in FIG. 4. During normal operation, the drug dosage is programmed or set by the physician and stored in memory of the drug dispenser. The dosage delivery algorithm determines if dosage delivery criteria are met in step S108, and the dosage is delivered in step S110 when the dosage delivery criteria are met. As noted above, the baseline dosage frequency can be continuous or intermittent.

If the patient is competent, the physician enables the patient activation function within programmed limits, e.g., how frequently a dosage may be delivered, both automatically and in response to patient activation, and the maximum dosage volume or bolus that can be delivered in a given time period. A drug dosage is delivered in step S110 when the patient activation is detected in step S100 and patient activation is so enabled as determined in step S102.

If an IHM 60 is implanted in the patient's body 10, the IHM 60 may at any time transmit a dosage command that is received by the external drug dispenser 40. Thus, a revised or adjusted dosage is stored in memory of the external drug dispenser 40 in step S106 when such a dosage command is received as determined in step S104. The adjusted dosage is then employed in steps S108 and S110 until a further adjusted dosage is received and stored in steps S104 and S106. The operating system of the external drug dispenser 40 may include an RF telemetry transceiver coupled to RF telemetry antenna 42 that transcutaneously transmits a confirmation of receipt of the adjusted dosage command to the IHM 60 in step S106.

In a special case, the baseline dosage delivered by the external drug dispenser 40 can be set to zero, and the adjusted dosage delivered in step S110 only when an adjusted dosage command is received in step S104 and stored in step S106. In this way, the sympatholytic cardiovascular agent is only delivered when the IHM dosage algorithm determines delivery to be appropriate, and the delivery continues until a subsequent adjusted dosage is calculated and transmitted to and received by the external drug dispenser 40 in step S104.

For example, if blood pressure and heart rate are determined to be within an unacceptable range, then the adjusted dosage would dictate delivery of a dosage or an increase in the delivery of the sympatholytic cardiovascular agent into the central nervous system. When the blood pressure and heart rate are determined subsequently to be within an acceptable range, then the adjusted dosage would dictate halt of delivery of the dosage or a decrease in the dosage of the sympatholytic cardiovascular agent delivered into the central nervous system.

Thus, the drug dosage is delivered in step S110 from time to time or continuously, depending upon the programmed or adjusted delivery frequency, when the delivery criteria are met in step S108 in the absence of either a patient activation or a received dosage command in steps S100–S106. In the simplest operating mode and embodiment of the invention, only steps S108 and S110 are performed between refills of the drug dispenser reservoir and patient work-ups by the attending physician.

The general operation of the IHM 50 in performing a dosage adjustment algorithm and communicating an adjusted dosage to the external drug dispenser (or a discrete IIP or IIP function incorporated into a combined IHM and IIP) is set forth in the steps of FIG. 5. The physiologic sensors, e.g., the activity sensor 106/152, the EGM processor 170 coupled to the sense electrodes 66, 68, and demodulator 150 coupled to the blood pressure sensor 64 of FIG. 3, are periodically activated and the sensor output signals are processed in step S200 to calculate the adjusted dosage.

The adjusted dosage is compared to the current dosage, that is the most recently determined dosage, and to programmed dosage limits in step S202. The adjusted dosage is communicated to the external drug dispenser 40 of FIG. 1 in step S210 if the adjusted dosage differs from the current dosage as determined in step S204 and the adjusted dosage is within programmed limits as determined in step S206. However, the adjusted dosage that is communicated in step S210 may be limited to one of the upper or lower dosage limits in step S208 in step S208 if the adjusted dosage satisfying step S204 is determined to beyond the programmed limits in step S206.

Figure 7:
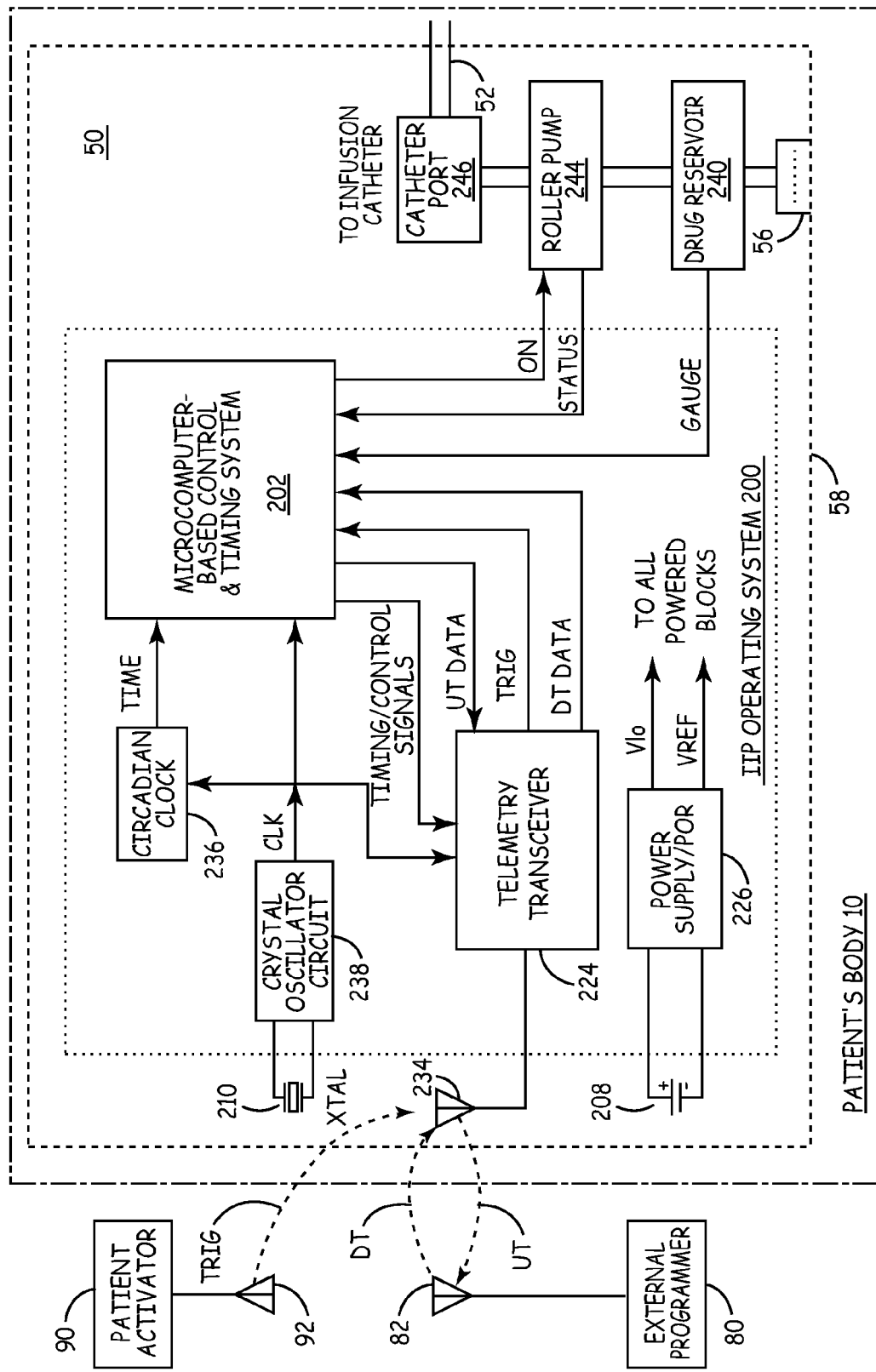
FIG. 7 is a simplified block diagram of the circuitry and components of the IIP of FIG. 6 communicating with the external programmer and optionally communicating with a patient activator operated by the patient.

An exemplary IIP system in which the present invention can be implemented comprising an IIP 50 implanted in the patient's body 10 that communicates by RF telemetry with an external programmer 80 and optionally communicating with a patient activator 90 operated by the patient is depicted in FIG. 6. A simplified block diagram of the circuitry and components of the IIP 50 of FIG. 6 that form the IIP operating system communicating with the external programmer 80 and optionally communicating with a patient activator 90 operated by the patient is depicted in FIG. 7. The IIP 50 includes the drug infusion catheter 52 coupled at a proximal end to a fitting of the IIP housing 58 and extending to the selected site in the central nervous system, e.g., the sub-arachnoid space described above with reference to FIG. 2.

As depicted in the above-referenced U.S. patent application Ser. No. 10/133,251 and the above-referenced '207 patent, the IIP housing 58 encloses an electronic control or operating system depicted in FIG. 6 including a control module 200 and associated electrical and mechanical components. The external programmer 50 and the patient activator 90 are also shown schematically in FIG. 7 disposed outside the patient's skin 12.

The mechanical components include a drug reservoir 240 associated with a resealable drug fill port 56 in the housing 58 and an outlet to a peristaltic roller pump 244. A bellows (not shown), associated with a gas-filled pressure chamber (not shown), applies a constant pressure against the drug reservoir 240 and the volume of drug within the drug reservoir 240. The catheter port 246 is coupled to the output of the peristaltic roller pump 246, and the roller pump 246 is periodically energized by an output signal of the circuit module 200 to deliver a dosage of the sympatholytic cardiovascular agent into the central nervous system through the drug infusion catheter 52. After subcutaneous implantation, a hypodermic needle is inserted through the patient's skin 12 and then through the resealable membrane of port 56 to fill the drug reservoir 240 with the sympatholytic cardiovascular agent.

The control module 200 is also coupled to a battery or batteries 208, an RF telemetry antenna 234, and a piezoelectric crystal 210. The control module 200 has a system architecture that is constructed about a microcomputer-based control and timing system 202 that varies in sophistication and complexity depending upon the type and functional features incorporated therein. The micro-computer-based IIP control and timing system 202 can be similar to the microcomputer circuit 114 of the IHM 60 described above with respect to FIG. 3. The functions of microcomputer-based IIP control and timing system 202 are controlled by firmware and programmed software algorithms stored in RAM and ROM including PROM and EEPROM and are carried out using a CPU, ALU, etc., of a typical microprocessor core architecture.

Power levels and signals are derived from battery 208 by the power supply/POR circuit 226 having power-on-reset (POR) capability to power the roller pump 244 and the other components of the circuit module 200. The power supply/POR circuit 226 provides one or more low voltage power Vlo and one or more VREF sources. Not all of the conventional interconnections of these voltage sources and signals with the circuitry of the IIP control module 200 are shown in FIG. 7.

In certain IIPs, an audible patient alert warning or message can be generated by a transducer when driven by a patient alert driver to advise of device operations, e.g., confirmed delivery of a bolus or dosage of sympatholytic cardiovascular agent, or the battery depletion level to warn of a depleted battery state or depletion of the sympatholytic cardiovascular agent in reservoir 240.

Current electronic IIP circuitry of control module 200 employs clocked CMOS digital logic ICs that require a clock signal CLK provided by a piezoelectric crystal 210 and system clock 238 coupled thereto. In FIG. 7, each CLK signal generated by system clock 238 is routed to all applicable clocked logic of the microcomputer-based control and timing system 202 and to the telemetry transceiver I/O circuit 224 and the circadian or real time clock 236. The crystal oscillator 238 provides one or more fixed frequency system clock or CLK signal that is independent of the battery voltage over an operating battery voltage range for system timing and control functions and in formatting uplink telemetry signal transmissions in the telemetry I/O circuit 224. The real-time or circadian clock 134 driven by system clock 238 that provides a time of day signal to the microcomputer-based timing and control system 202.

The telemetry transceiver 224 is coupled to the RF telemetry antenna 234 and operates in a manner similar to the telemetry transceiver 136 of the IHM 60 described above with reference to FIG. 3. The telemetry transceiver 224 enables UT and DT telemetry capabilities with a remotely located external medical device, e.g., programmer 80, or a more proximal external medical device carried on the patient's body 10, or another IMD in the patient's body 10. During an UT transmission, the external RF telemetry antenna 82 of programmer 80 operates as a telemetry receiver antenna, and the IIP RF telemetry antenna 234 operates as a telemetry transmitter antenna. Conversely, during a DT transmission, the external RF telemetry antenna 82 operates as a telemetry transmitter antenna, and the IIP RF telemetry antenna 234 operates as a telemetry receiver antenna. Data to be UT transmitted in response to a DT transmitted interrogation command is In general terms, the operation of the roller pump 244 can controlled through resident software and firmware in the microcomputer-based control and timing system 202 in a general manner similar to that described in commonly assigned U.S. Pat. No. 4,692,147. The frequency and volume of each bolus or dosage of sympatholytic cardiovascular agent delivered into the intrathecal space can be governed by DT transmitted dosage commands that are stored in RAM. Data related to the delivery of dosages of sympatholytic cardiovascular agent can be stored in RAM within the microcomputer-based control and timing system 202 and UT transmitted to the programmer 80 in a telemetry session initiated by a medical care provider.

There are a number of ways that the IIP 60 can employed to dispense sympatholytic cardiovascular agent into the central nervous system in accordance with the various aspects of the invention. First, a fixed amount or bolus or dosage can be dispensed at predetermined timed intervals over the entire 24 hour day, that is once a day or more than once a day to maintain a relatively uniform level of sympatholytic cardiovascular agent in the central nervous system in the CSF. Or, a bolus or dosage of sympatholytic cardiovascular agent into the central nervous system may be delivered at specific times as timed out by the circadian clock 236.

The patient's physician would develop a conservative delivery regimen and use the programmer 80 to DT transmit the delivery times or delivery delay and bolus or dosage quantities. The symptoms of HF or pathologies associated with HF would be monitored, and the physician would periodically adjust the bolus or dosage depending upon the observed response or lack of response.

Optionally, the patient can be provided with the patient activator 90 to command the delivery of a bolus sympatholytic cardiovascular agent into the central nervous system. Suitable patient activators can communicate with IMDs, e.g., IIP 50, through the use of digitally encoded RF telemetry, infrared, acoustic pulsed, or magnetic signals that pass through the patient's skin 12. Preferably, the patient activator 90 depicted in FIGS. 6 and 7 is of the type disclosed in commonly assigned U.S. Pat. No. 5,755,737 or in U.S. Pat. Nos. 5,674,249 and 4,263,679 that communicate with the IIP 60 via RF telemetry transmissions through the patient's skin 12 between the patient activator antenna 92 and the IIP RF antenna 234.

For simplicity, the depicted exemplary patient activator 90 includes a battery powered RF telemetry transmitter conforming to the RF telemetry protocol employed in RF telemetry between the RF telemetry transceiver 224 and the telemetry transceiver within the programmer 80. The patient activator 90 preferably includes a button 94 to be depressed by the patient to cause an RF activation or TRIG signal to be emitted from the RF antenna 92 that is received by the RF telemetry transceiver 224. A first light, e.g., an LED 96, lights up when the TRIG signal is transmitted. A second light, e.g., LED 98, may be provided to indicate patient activator battery status.

The TRIG signal is received via RF antenna 234 and transmitted through RF telemetry transceiver 224 to the microcomputer-based control and timing system 202. In accordance with this aspect of the present invention, a motivated and competent patient provided with a patient activator 90 can transmit the TRIG signal and command the control and timing system 202 to deliver a bolus or dosage of sympatholytic cardiovascular agent when the patient experiences symptoms or preceding an activity that might cause symptoms.

The frequency of delivery or discharge of dosages of sympatholytic cardiovascular agent can be limited within a delivery delay time window started by any delivery earlier initiated by the patient. In other words, the receipt of a TRIG command from the patient activator 90 would initiate delivery of the bolus of sympatholytic cardiovascular agent and also start a delivery delay timer that would have to time out before the control and timing system 202 can respond to any further TRIG commands initiated by the patient's use of the magnet patient activator 90.

The delivery of sympatholytic cardiovascular agent into the central nervous system is alternatively controlled in a variety of ways. Returning to FIG. 4, the steps S100, S102, S108 and S110 are followed in the same manner as described above. During normal operation, the drug dosage is programmed by the physician employing programmer 80 and stored in IIP memory. The dosage delivery algorithm determines if dosage delivery criteria are met in step S108, and the dosage is delivered in step S110 when the dosage delivery criteria are met. As noted above, the dosage frequency can be continuous or intermittent.

If the patient is competent, the physician enables the patient activation function of the patient activator 90 within programmed limits, e.g., how frequently a dosage may be delivered, both automatically and in response to patient activation, and the maximum dosage volume or bolus that can be delivered in a given time period. A drug dosage is delivered in step S110 when the patient activation is detected in step S100 and patient activation is so enabled as determined in step S102.

Thus, the drug dosage is delivered in step S110 from time to time or continuously, depending upon the programmed or adjusted delivery frequency, when the delivery criteria are met in step S108 in the absence of a patient activation in step S102. In the simplest operating mode and embodiment of the invention, only steps S108 and S10 are performed between refills of the IIP drug reservoir 240 and patient work-ups by the attending physician.

Figure 9:
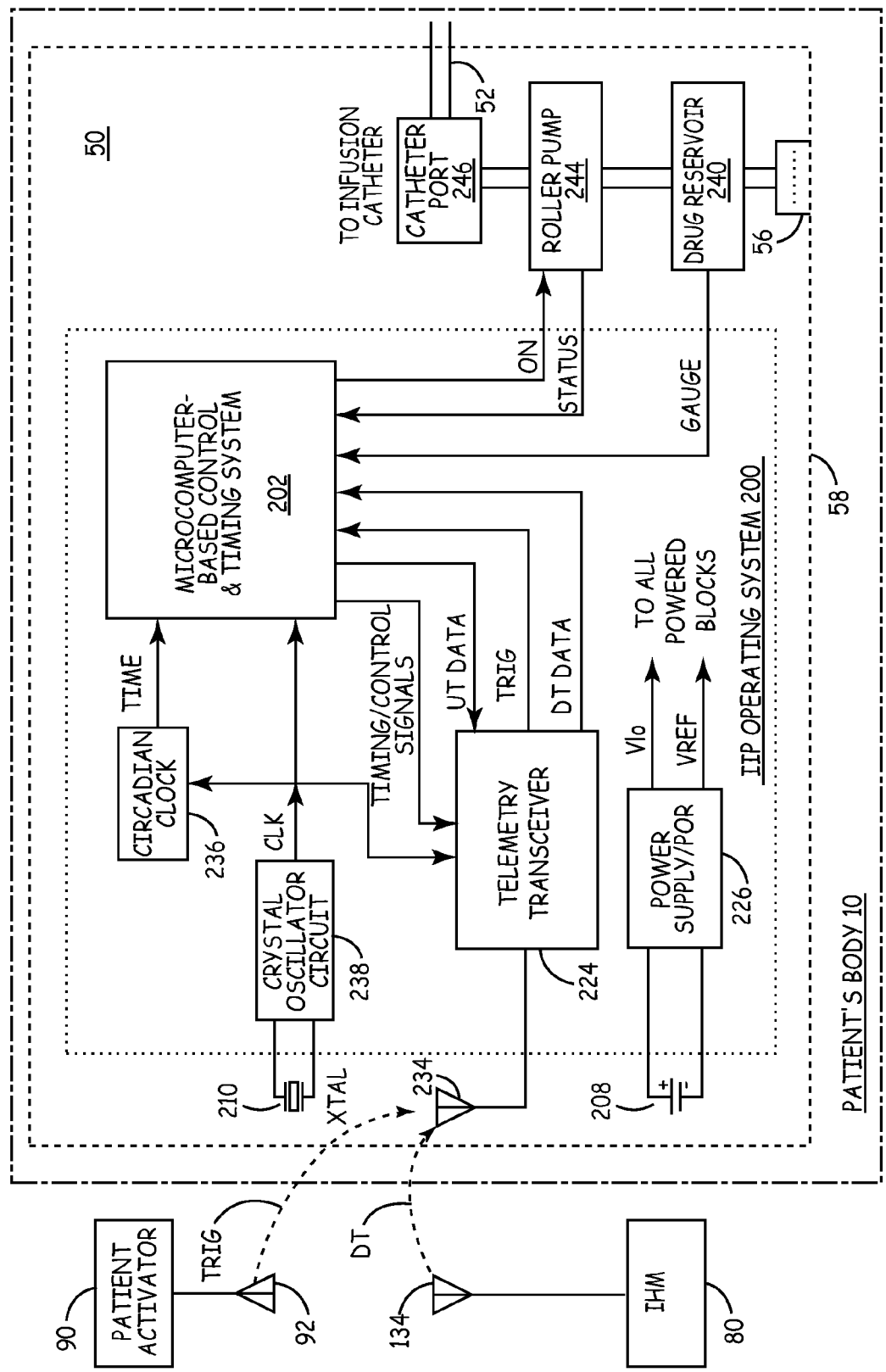
FIG. 9 is a simplified block diagram of the circuitry and components of the IIP of FIG. 8 communicating with the IHM, the external programmer, and optionally communicating with a patient activator operated by the patient.

A further exemplary IIP system in which the present invention can be implemented comprising a discrete IIP 50 implanted in the patient's body 10 that communicates by RF telemetry with a discrete IHM 60 that is also implanted in the patient's body 10 and optionally communicates with a patient activator 90 operated by the patient is depicted in FIGS. 8 and 9. In this IIP system, both of the IIP 50 and the IHM 60 communicate with an external programmer 80 via UT and DT transmissions as described above.

The IHM 60 is configured as described above in reference to FIG. 3 and performs the steps of FIG. 5 as described above. In this embodiment, the IHM 60 develops a dosage command DC following steps S200–S208 of FIG. 5 and transmits the dosage command DC to the IIP 50 in step S210. The adjusted dosage and related physiologic sensor and other data are stored in step S212 for later UT transmission to external programmer 80.

Referring to FIG. 9, the IIP 50 is configured as described above with respect to FIG. 7 to perform the steps of FIG. 4 as described above; in this embodiment, the RF telemetry transceiver 224 receives, decodes and passes the dosage command DC received in step S104 of FIG. 4 to the microcomputer-based timing and control system 202.

Figure 11:
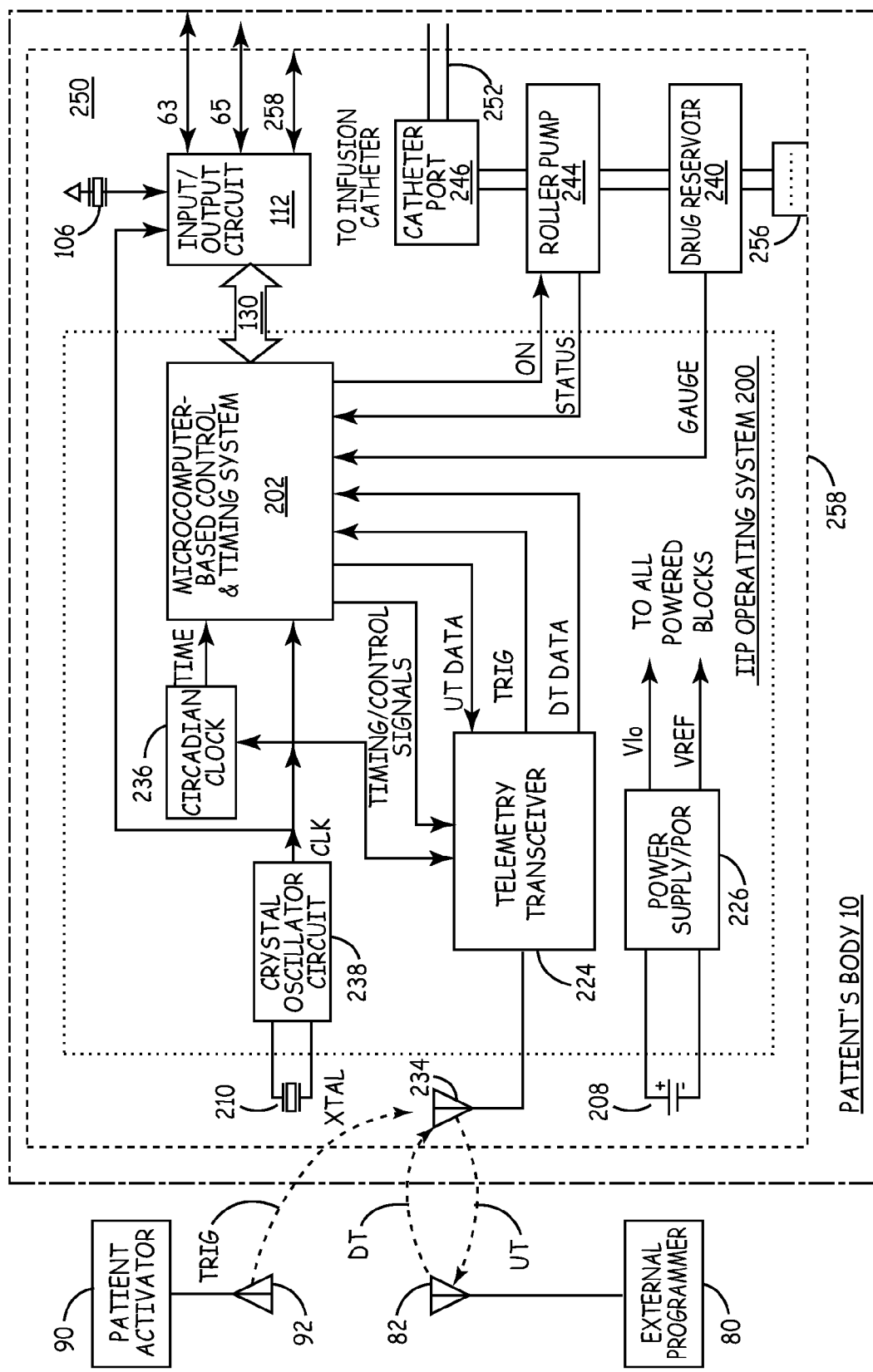
FIG. 11 is a simplified block diagram of the circuitry and components of the combined IHM and IIP of FIG. 10 communicating with the external programmer and optionally communicating with a patient activator operated by the patient.

A still further exemplary IIP system in which the present invention can be implemented is depicted in FIGS. 10 and 11 comprising a combined IIP and IHM 250 implanted in the patient's body 10 that communicates by RF telemetry with external programmer 80 via UT and DT transmissions as described above. The IIP and IHM 250 optionally communicates with a patient activator 90 operated by the patient as described above with respect to FIGS. 8 and 9 and functions in accordance with the steps of FIG. 12. The combined IIP and IHM 250 is coupled by suitable connectors to the proximal ends of the drug infusion catheter 52 and the cardiac lead 62 described above.

Thus, the combined IIP and IHM 250 incorporates the physical structure of the IIP 50 with the input/output circuit 112 of the IHM depicted in FIG. 3 and described above. The housing 258 of the IIP and IHM 250 is connected to the input/output circuit 112 to function as an indifferent EGM sense electrode and to the cardiac lead conductors 63 and 65 as described above with respect to FIG. 3 The pressure and temperature signals are detected through the electrical conductors 63 and 65 extending through an insulating lead body to the distal pressure and temperature sensor 64 and distal sense electrode 66 within the right ventricle (RV) of heart 30. The EGM is sensed between the active distal tip electrode 66 and the indifferent electrode formed by the hermetically sealed monitor housing 258 as described above.

Figure 12:
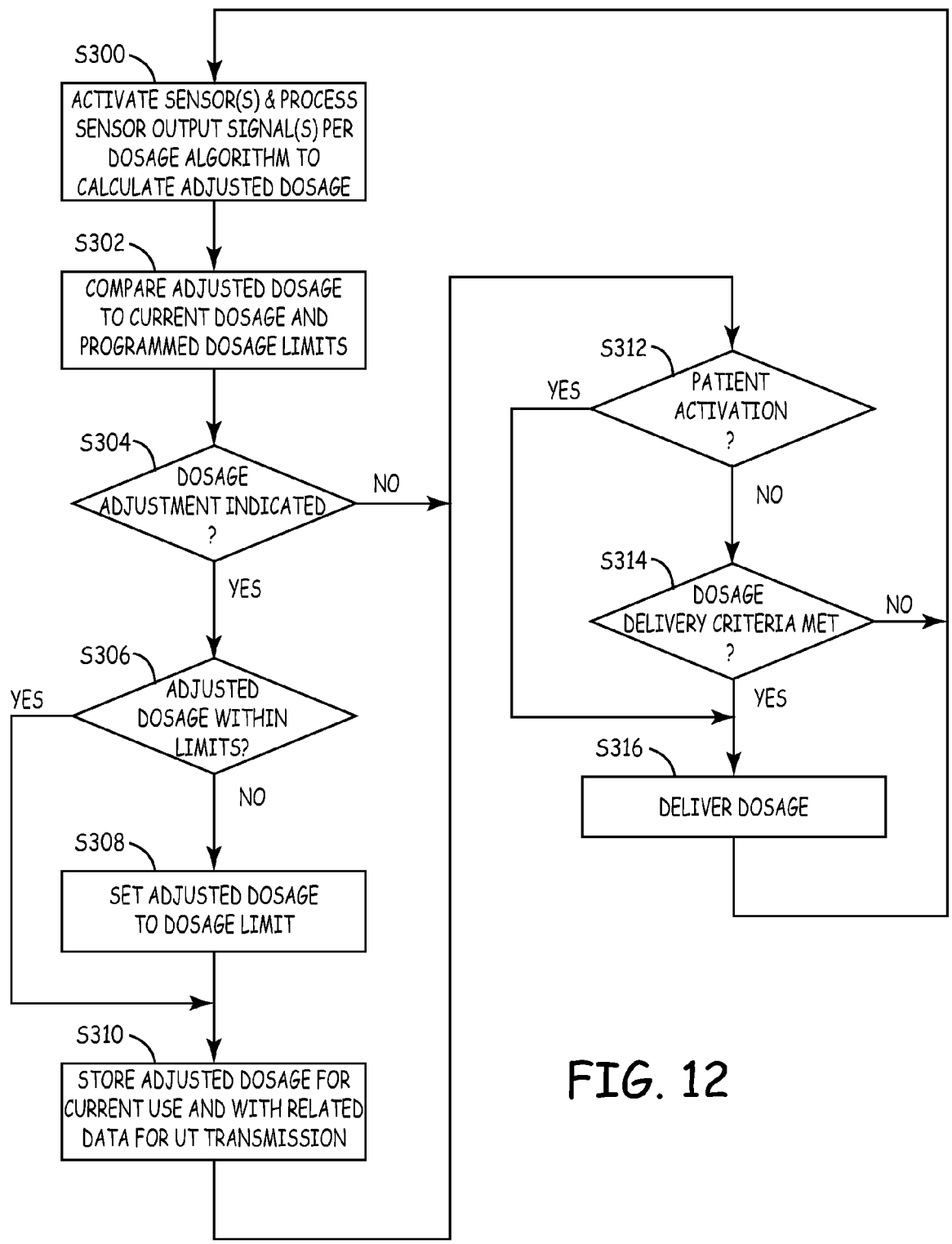
FIG. 12 is a simplified flow chart of the steps of operation of the combined IHM and IIP of FIGS. 10 and 11.

The micro-computer-based timing and control system 202 and the input/output circuit 112 perform the dosage adjustment and delivery algorithm depicted in the steps of FIG. 12. In this embodiment, the micro-computer-based timing and control system 202 processes the signals developed in the input output circuit 112 received through data communication bus 130 to perform steps S300-S308 in the same manner as steps S200–S208 of FIG. 5 as described above to determine an adjusted dosage, if any is dictated by steps S304-S308. The adjusted dosage is stored in RAM for use as the current dosage and for UT transmission upon receipt of a DT transmitted interrogation command from programmer 80. The micro-computer-based timing and control system 202 performs the steps S312 and S314 in the same fashion as steps S100 and S102 of FIG. 4 as described above, and the dosage is delivered in step S316 in the manner of step S10 of FIG. 4 as described above.

Thus, a variety of embodiments are presented that facilitate detecting symptoms of pathologies associated with HF and triggering delivery of a sympatholytic cardiovascular agent to a central nervous system site to alleviate such symptoms and otherwise treat HF and pathologies associated with HF.

The sympatholytic cardiovascular agent is preferably delivered to treat any disease process that involves overactivity of the sympathetic nervous system comprising the specific cardiovascular indications: angina, hypertension, HF, coronary artery disease, and cardiac arrhythmias. In addition, the sympatholytic cardiovascular agent can be delivered to treat cardiovascular-related diseases in which the sympathetic nervous system is overactive such as major depression and sleep apnea.

Preferably, the sympatholytic cardiovascular agent is one of the group consisting of an alpha-adrenergic agonist and an alpha2-adrenergic agonist, e.g., clonidine, p-aminoclonidine, guanabenz, lidamidine, tizanidine, moxonidine, methyldopa, xylazine, guanfacine, detomidine, medetomidine, and dexmedetomidine.

In one example, clonidine may be delivered from the IIP into the central nervous system by continuous intrathecal infusion at a dosage of 0.01 to 1.0 mg/day or by continuous intrathecal infusion at a dosage of 50 to 500 mcg/day or by continuous intrathecal infusion at a dosage of 100 to 400 mcg/day. The clonidine formulation may comprise clonidine hydrochloride at a concentration of 0.5 to 10 mg/mL in a vehicle (solvent) comprising sterile water or 0.9% sodium chloride solution that is preferably free of preservatives and has a tonicity of 300±50 mOsm/L.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

It will also be understood that there may be other structures, functions and operations ancillary to the typical operation of the above-described devices are not disclosed and are not necessary to the practice of the present invention.

In addition, it will be understood that specifically described structures, functions and operations set forth in the above-referenced patents can be practiced in conjunction with the present invention, but they are not essential to its practice.

One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. A method of delivering a drug dosage from a drug dispenser to receptors of the central nervous system of a patient's body to therapeutically treat one of pre-existing symptoms of heart failure ("HF") and pre-existing pathologies associated with HF, the method comprising the steps of:
   surgically implanting a drug infusion catheter with a distal drug delivery portion disposed at a predetermined central nervous system site;
   coupling a proximal end of the drug infusion catheter to a drug delivery pump;
   monitoring the patient for at least one pre-existing of symptoms of HF and pre-existing pathologies associated with HF; and
   in response to a positive detection of one pre-existing of HF and pre-existing pathologies associated with HF, operating the drug delivery pump to discharge a predetermined dosage of a sympatholytic cardiovascular agent to a central nervous system site effective to alleviate at least one of the pre-existing symptoms of HF and the pre-existing pathologies associated with HF.

2. A method according to claim 1, further comprising:
   surgically implanting a physiologic sensor in the patient's body;
   operating the physiologic sensor to derive a physiologic parameter associated with HF or a pathology associated with HF; and
   adjusting the dosage as a function of the monitored physiologic parameter associated with HF or a pathology associated with HF.

3. A method according to claim 2, wherein the physiologic sensors comprise one or more of an EGM sensor, a patient activity sensor, a cardiac mechanical function metric determining sensor, a blood chemistry sensor, an arterial, venous or heart chamber blood pressure sensor, a blood temperature sensor, a neural activity sensor, and a molecular probe.

4. A method according to claim 3, wherein the operating step further comprises determining one or more of heart rate, heart rate variability, and aberrations in the PQRST segment include changes in morphology, ST segment elevation, electrical alternans, and interval changes associated with HF or a pathology associated with HF.

5. A method according to claim 4, wherein the sympatholytic agent comprises one of the group consisting of an alpha-adrenergic agonist and an alpha2-adrenergic agonist.

6. A method according to claim 4, wherein the sympatholytic agent consists of clonidine.

7. A method according to claim 3, wherein the sympatholytic agent comprises one of the group consisting of an alpha-adrenergic agonist and an alpha2-adrenergic agonist.

8. A method according to claim 3, wherein the sympatholytic agent consists of clonidine.

9. A method according to claim 2, wherein the sympatholytic agent comprises one of the group consisting of an alpha-adrenergic agonist and an alpha2-adrenergic agonist.

10. A method according to claim 2, wherein the sympatholytic agent consists of clonidine.

11. A method according to claim 1, wherein the sympatholytic agent comprises one of the group consisting of an alpha-adrenergic agonist and an alpha2-adrenergic agonist.

12. A method according to claim 11, wherein the physiologic sensors comprise one or more of an EGM sensor, and the operating step further comprises determining one or more of heart rate, heart rate variability, and aberrations in the PQRST segment include changes in morphology, ST segment elevation, electrical alternans, and interval changes associated with HF or a pathology associated with HF.

13. A method according to claim 1, wherein the sympatholytic agent consists of clonidine.

14. A method according to claim 13, wherein the physiologic sensors comprise one or more of an EGM sensor, and the operating step further comprises determining one or more of heart rate, heart rate variability, and aberrations in the PQRST segment include changes in morphology, ST segment elevation, electrical alternans, and interval changes associated with HF or a pathology associated with HF.

15. A method according to claim 1, wherein the sympatholytic cardiovascular agent is preferably delivered into the central nervous system accessed at one of: the sub-arachnoid space; the sub-arachnoid space of the spinal cord; the sub-arachnoid space of the thoracic spinal cord; the sub-arachnoid space between the first and fifth thoracic vertebrae; the sympathetic preganglionic cell bodies located in the intermediolateral cell column of the spinal cord; the preganglionic sympathetic neurons which provide innervation to the heart; and the preganglionic sympathetic neurons which provide innervation to the kidneys.

16. A method according to claim 15, wherein the sympatholytic agent comprises one of the group consisting of an alpha-adrenergic agonist and an alpha2-adrenergic agonist.

17. A method according to claim 15, wherein the sympatholytic agent comprises one of the group consisting of clonidine, p-aminoclonidine, guanabenz, lidamidine, tizanidine, moxonidine, methyldopa, xylazine, guanfacine, detomidine, medetomidine, dexmedetomidine, lidocaine, bupivacaine, and ropivacaine.

18. A method according to claim 1, wherein the drug delivery pump comprises an externally worn drug pump coupled to the proximal end of the drug infusion catheter.

19. A method according to claim 18, further comprising:
   surgically implanting a physiologic sensor in the patient's body;
   operating the physiologic sensor to derive a physiologic parameter associated with HF or a pathology associated with HF; and
   adjusting the dosage as a function of the monitored physiologic parameter associated with HF or a pathology associated with HF.

20. A method according to claim 18, wherein the sympatholytic agent comprises one of the group consisting of an alpha-adrenergic agonist and an alpha2-adrenergic agonist.

21. A method according to claim 18, wherein the sympatholytic agent comprises one of the group consisting of clonidine, p-aminoclonidine, guanabenz, lidamidine, tizanidine, moxonidine, methyldopa, xylazine, guanfacine, detomidine, medetomidine, dexmedetomidine lidocaine, bupivacaine, and ropivacaine.

22. A method according to claim 1, wherein the drug delivery pump comprises an implantable infusion pump coupled to the proximal end of the drug infusion catheter.

23. A method according to claim 22, further comprising:
   surgically implanting a physiologic sensor in the patient's body;
   operating the physiologic sensor to derive a physiologic parameter associated with HF or a pathology associated with HF; and
   adjusting the dosage as a function of the monitored physiologic parameter associated with HF or a pathology associated with HF.

24. A method according to claim 23, further comprising providing the patient with a patient activator whereby the operating step comprises operating the patient activator to command the delivery of a dosage of the sympatholytic cardiovascular agent to a the central nervous system site.

25. A method according to claim 22, further comprising providing the patient with a patient activator whereby the operating step comprises operating the patient activator to command the delivery of a dosage of the sympatholytic cardiovascular agent to a the central nervous system site.

26. A method according to claim 22, wherein the sympatholytic agent comprises one of the group consisting of an alpha-adrenergic agonist and an alpha2-adrenergic agonist.

27. A method according to claim 22, wherein the sympatholytic agent consists of clonidine.

28. A method according to claim 1 wherein the central nervous system site comprises one of: the sub-arachnoid space; the sub-arachnoid space of the spinal cord; the sub-arachnoid space of the thoracic spinal cord; the sub-arachnoid space between the first and fifth thoracic vertebrae; the sympathetic preganglionic cell bodies located in the intermediolateral cell column of the spinal cord; the preganglionic sympathetic neurons that provide innervation to the heart; and the preganglionic sympathetic neurons that provide innervation to the kidneys.

29. A method according to claim 28, wherein the sympatholytic agent comprises one of the group consisting of an alpha-adrenergic agonist and an alpha2-adrenergic agonist.

30. A method according to claim 28, wherein the sympatholytic agent consists of clonidine.

31. A method according to claim 28, wherein the sympatholytic agent comprises clonidine delivered from into the central nervous system by continuous intrathecal infusion at a dosage of 0.01 to 1.0 mg/day.

32. A method according to claim 28, wherein the sympatholytic agent comprises clonidine delivered from into the central nervous system by continuous intrathecal infusion at a dosage of 0.01 to 1.0 mg/day.

33. A method according to claim 28, wherein the sympatholytic agent comprises clonidine delivered from into the central nervous system by continuous intrathecal infusion at a dosage of 50 to 500 mcg/day.

34. A method according to claim 28, wherein the sympatholytic agent comprises clonidine delivered from into the central nervous system by continuous intrathecal infusion at a dosage of 100 to 400 mcg/day.

35. A method according to claim 1, wherein the sympatholytic agent comprises clonidine delivered from into the central nervous system by continuous intrathecal infusion at a dosage of 0.01 to 1.0 mg/day.

36. A method according to claim 1, wherein the sympatholytic agent comprises clonidine delivered from into the central nervous system by continuous intrathecal infusion at a dosage of 50 to 500 mcg/day.

37. A method according to claim 1, wherein the sympatholytic agent comprises clonidine delivered from into the central nervous system by continuous intrathecal infusion at a dosage of 100 to 400 mcg/day.

* * * * *